:::: {.flex-row}

::::

US007767149B2

(12) United States Patent
Maus et al.

(10) Patent No.: US 7,767,149 B2
(45) Date of Patent: Aug. 3, 2010

(54) HEALTH MONITORING AND DIAGNOSTIC DEVICE AND NETWORK-BASED HEALTH ASSESSMENT AND MEDICAL RECORDS MAINTENANCE SYSTEM

(75) Inventors: Christopher T. Maus, Sagle, ID (US); Craig A. Coad, Cataldo, ID (US); Jackson B. Connolly, Post Falls, ID (US); Noah M. Coad, Cataldo, ID (US); James L. Moody, Wilsonville, OR (US); Kenn A. Nesbitt, Spokane, WA (US); Kenneth D. Clegg, Mead, WA (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 1160 days.

(21) Appl. No.: 10/649,293

(22) Filed: Aug. 26, 2003

(65) Prior Publication Data
US 2004/0037738 A1 Feb. 26, 2004

Related U.S. Application Data

(62) Division of application No. 09/436,323, filed on Nov. 8, 1999, now Pat. No. 6,602,469.

(60) Provisional application No. 60/107,707, filed on Nov. 9, 1998, provisional application No. 60/144,705, filed on Jul. 20, 1999.

(51) Int. Cl.
*G01N 33/00* (2006.01)
(52) U.S. Cl. ..................... 422/68.1; 600/309; 600/310
(58) Field of Classification Search ............. 422/68.1, 422/811; 600/309, 310
See application file for complete search history.

(56) References Cited

U.S. PATENT DOCUMENTS 4,706,275 A   11/1987   Kamil (Continued)

FOREIGN PATENT DOCUMENTS

WO   WO 94/19684   9/1994

(Continued)

OTHER PUBLICATIONS

Author: Deborah Ann Adams, PhD, RN, Madge Buus-Frank, MS, RN, ARNP Title: Point-of-Care Technology: The i-STAT™ System for Bedside Blood Analysis (Journal of Pediatric Nursing, vol. 10, No. 3) Date: Jun. 1995.

(Continued)

*Primary Examiner*—Sam P Siefke
(74) *Attorney, Agent, or Firm*—Patton Boggs LLP

(57) ABSTRACT

A health monitoring and diagnostic device (LIFESTREAM cholesterol meter) configured as a self-contained testing and diagnostic unit in a clam-shell type case. One side of the case includes a spring-loaded finger stick and a compartment for carrying one or more packages of disposable items including a test strip, a needle for the finger stick, and an alcohol swipe. The other half of the case includes a test strip reader, a key pad, and a liquid crystal display. The meter reads a test strip carrying a droplet of blood and receives additional diagnostic information from the patient, such as age, gender, weight, and family history of heart disease. Within minutes, the meter displays test results, including total cholesterol levels. The meter also displays additional diagnostic results, such as the patient's "cardiac age," recommended weight loss, and a cardiac risk assessment. The meter also works in connection with a network-based comprehensive health analysis and reporting system. The meter writes patient data to a smartcard. This patient data typically includes patient identification information, the test results, the diagnostic information, and the diagnostic results. A computer station reads the smartcard and establishes a network connection with a health report server over the Internet. The computer then downloads the patient data to the health report server, which prepares a comprehensive health report. Within minutes, this report is transmitted back to the computer station, where it is printed out and delivered to the patient.

8 Claims, 30 Drawing Sheets

U.S. PATENT DOCUMENTS

| | | | |
|---|---|---|---|
| 4,975,647 | A | 12/1990 | Downer et al. |
| 5,053,199 | A | 10/1991 | Keiser et al. |
| 5,258,906 | A | 11/1993 | Kroll et al. |
| 5,307,263 | A * | 4/1994 | Brown .................. 600/301 |
| 5,396,886 | A * | 3/1995 | Cuypers ................ 600/301 |
| 5,724,580 | A * | 3/1998 | Levin et al. ............ 707/104.1 |
| 5,780,304 | A | 7/1998 | Matzinger et al. |
| 5,822,715 | A | 10/1998 | Worthington et al. |

FOREIGN PATENT DOCUMENTS

| | | |
|---|---|---|
| WO | WO 96/41288 | 12/1996 |
| WO | WO 98/15910 | 4/1998 |
| WO | WO 98/24358 | 6/1998 |

OTHER PUBLICATIONS

Author: Nelson L. Alpert, Ph.D, *Editor* Title: i-STAT™ Point-of-Care Testing System (Clinical Instrument Systems (CIS), vol. 13, No. 4 p. 1-7) Date: Unknown.

Author: Jane Grimson, (*Member, IEEE*), William Grimson, Damon Berry, Gaye Stephens, Eoghan Felton, Dipak Kalra, Pieter Toussaint, and Onno W. Weier Title: A CORBA-Based Integration of Distributed Electronic Healthcare Records Using the Synapses Approach (IEEE Transaction on Information Technology in Biomedicine> vol. 2 No. 3) Date: Sep. 1998.

Author: Lifestream Technologies, Inc. Title: LFST Signs Development and Production Agreement with Boehringer Mannheim (www.lifestreamtech.com) Date: Mar. 11, 2000.

Author: Despina Polemi, *Institute of Communications and Computer Systems, National Technical University of Athens, Heroon Polytechniou 9*, Zografou, Athens, Greece Title: Trusted Third Party Services for Health care in Europe (Future Generation Computer Systems 14 51-59) (BNS p. 1-9) Date: © 1998 Elsevier Science B.V. All rights reserved.

Author: Lifestream Technologies, Inc. Title: FDA Clears New Hand-Held Instrument to Screen and Monitor Cholesterol (Healthcare Professionals Use Lifestream Technologies Cholestron Pro to Monitor Treatment Programs That Reduce Risk of Developing Coronary Heart Disease) (www.lifestreamtech.com) Date: Mar. 11, 2000.

* cited by examiner 2108  2200  2202

| Address | Billing Info | Cover Letter |

Billing Method   [Credit Card ▼]

― Credit Card Information ―

Credit Card Number [          ]   Expiration Date [     ]

Name on card [          ]

― Checking Account Information ―

Checking Account [          ]   Routing Number [     ]

[💾 Save]

Questionnaire Data

Patient

| File Number | First | Last | Test Time Stamp |
|---|---|---|---|
| 123 | Jill | Smith | 12/8/98 10:16:01AM |

Risk Components

- Family History ☑
- Personal History ☐
- CVD ☐
- AF ☐
- LVH ☐
- Diabetes Type 1 ☐
- Diabetes Type 2 ☐
- Smoker ☑

| | | |
|---|---|---|
| Height | 68 | inches |
| Weight | 165 | pounds |
| Age | 48 | Years |
| Chol | 215 | mg/dl |
| Trig | 0 | mg/dl |
| LDL | 0 | mg/dl |
| HDL | 0 | mg/dl |

| | | |
|---|---|---|
| Glucose | 0 | mg/dl |
| Body Fat | 24 | % |
| Systolic | 140 | |
| Diastolic | 80 | |
| Fitness | Sedentary | |
| Ethnicity | Caucasian | |

Gender: ○ Male  ⊙ Female

Record 1 of 1 — Read SmartCard — Save

Previous | Next

FIG. 26

|  | CORONARY RISK FACTORS | TEST RESULTS | IDEAL RANGE | GOALS |
|---|---|---|---|---|
|  | GENDER | MALE |  |  |
| IDEAL | PERSONAL HISTORY | NO | NONE |  |
| IDEAL | FAMILY HISTORY | NO | NONE |  |
|  | CVD | NO |  |  |
|  | AF | NO |  |  |
|  | LVH | NO |  |  |
| MODERATE | DIABETES (TYPE 1) | YES | NONE |  |
| HIGH | SMOKER | YES | NO |  |
|  | HEIGHT | 66 in |  |  |
|  | WEIGHT | 155 lbs |  |  |
|  | AGE | 44 |  |  |
| MODERATE | TOTAL CHOLESTEROL | 211 | < 200 |  |
|  | TRIGLYCERIDES | 200 |  |  |
|  | HDL | N/A | 45-65 |  |
|  | LDL | N/A | 65-135 |  |
|  | GLUCOSE | N/A |  |  |
| IDEAL | PERCENTAGE OF BODY FAT | N/A | 18% |  |
| IDEAL | BP SYSTOLIC | 115 | < 120 |  |
| LOW | BP DIASTOLIC | 80 | < 80 |  |
| LOW | FITNESS | MODERATE | HIGH |  |

2802

| PERSONAL HEALTH CONSEQUENCES | | |
|---|---|---|
| BODY MASS INDEX (BMI) | 25 | < 25 |
| POUNDS OVERWEIGHT | 0 | 0 |
| CHOLESTEROL/HDL RATIO | N/A:1 | < 3.5:1 |
| CARDIAC RISK | 5 YEARS - 5%  10 YEARS - 10% | |
| BIOLOGICAL AGE | 47 | < 44 |
| STROKE RISK | 10 YEARS - LOW RISK | |

2804

EXTENDED HEALTH ASSESSMENT SUMMARY        2806

| CHRONOLOGICAL AGE | 30 | 40 | 50 | 60 | 70 |
|---|---|---|---|---|---|
| CARDIAC AGE | N/A | N/A | 52 | 62 | 69 |

FIG. 28

HEALTH MONITORING AND DIAGNOSTIC DEVICE AND NETWORK-BASED HEALTH ASSESSMENT AND MEDICAL RECORDS MAINTENANCE SYSTEM

REFERENCE TO RELATED APPLICATIONS

This application is a divisional of U.S. patent application Ser. No. 09/436,323 filed Nov. 8, 1999, now U.S. Pat. No. 6,602,469 issued Aug. 5, 2003; which claims the benefit of commonly-owned U.S. Provisional Patent Application No. 60/107,707, filed Nov. 9, 1998; and commonly-owned U.S. Provisional Patent Application No. 60/144,705, filed Jul. 20, 1999.

TECHNICAL FIELD

This invention relates to health monitoring and diagnostic devices and, more particularly, relates to a hand-held device operable for determining blood lipid levels from test-strip analyses, obtaining additional diagnostic information from a user, displaying corresponding diagnostic results, and storing this data on a secure patient-held data carrier, such as a smart-card. The invention also relates to a secure network-based health assessment and medical records maintenance system that receives medical information from the health monitoring and diagnostic devices, produces health assessments based on the received medical information, and stores the received medical information in a secure medical records maintenance system.

BACKGROUND OF THE INVENTION

American health care is undergoing a revolution. By the year 2000, more than two-thirds of all American workers with health insurance will be enrolled in some kind of managed care plan, where the emphasis is on early detection of disease and preventive care.

Fueling this revolution is the skyrocketing cost of health care, combined with new medical research showing lifestyle is important to good health. In fact, in its 1982 report on "Health and Behavior," the National Academy of Sciences concluded that half of the ten leading causes of death in the United States are primarily related to lifestyle. Dietary patterns are identified as key lifestyle choices.

Cholesterol levels are particularly important in the United States. For this reason, the American Heart Association, the American Medical Association and the health related agencies of the U.S. government have embarked on national education campaigns to inform the public about the importance of making lifestyle changes to lower blood cholesterol and prevent heart disease. Although the dangers of high cholesterol have been widely publicized, many people fail to make effective use of this information because they do not know their own blood cholesterol levels. In other words, a great many of the people with high cholesterol levels fail to heed the advice to lower their cholesterol levels simply because they are unaware of their own cholesterol levels.

This situation persists because of the high cost and inconvenience presently involved in obtaining cholesterol information. To obtain this information, most people go to a physician's office, have blood drawn, and wait for the return of the blood chemistry analysis. Often, obtaining the results involves a second trip to the physician's office. This is expensive and time consuming; the average cost is about $83 for each office cholesterol consultation, and the average wait for the results is several days.

The cost and inconvenience involved in obtaining cholesterol tests inhibits many people from testing their cholesterol frequently enough to provide effective positive feedback. As a result, many people who begin corrective exercise, diet, or drug therapy programs in response to high cholesterol tests often give up their corrective programs because they do not monitor their cholesterol frequently enough to remain aware of the benefits of their programs. Moreover, blood cholesterol numbers by themselves are often poor motivators for patients who feel and look fine, and do not immediately feel or look differently when they take their prescriptions. In fact, studies have shown that 80% of the patients prescribed cholesterol-lowering drug therapies stop taking their prescriptions within a few months. And the attrition rates for exercise and diet programs may be even higher.

In addition, there is a need for a medical records maintenance system, not only for blood cholesterol tests but for many types of medical information that can be obtained outside of the hospital environment. This need will increase with increases in the availability of remote health monitoring devices in the future, such as blood pressure measuring devices, blood sugar testing devices, blood cholesterol testing devices, AIDS testing devices, heart monitoring devices, sleep respiration monitoring devices, reproductive cycle and pregnancy monitoring devices, epileptic and other types of seizure monitoring devices, and a wide range of other remote health monitoring devices that may be developed in the future. As the availability of the remote health monitoring devices increases, users will have an increasing need for securely storing the tests results in electronic format. The current system of hard-copy and electronic medical records maintained in doctors' offices will become increasingly obsolete and inconvenient as the availability of electronically-stored medical data increases. Because a patient's medical records are highly confidential, there is a need for a highly secure and permanent medical records maintenance system under the control of individual patients and their doctors.

Thus, there is a general need in the art for a less expensive and more convenient approach to providing cholesterol tests. There is a further need for making motivational information regarding cholesterol levels more readily available and more effective. And there is yet another need for a highly secure and permanent medical records maintenance system under the control of individual patients and their doctors.

SUMMARY OF THE INVENTION

The present invention meets the needs described above in a health monitoring and diagnostic device referred to as a LIFESTREAM cholesterol meter. This meter is configured as a self-contained testing and diagnostic unit in a clam-shell type case. One side of the case includes a biological sample gathering device, such as spring-loaded finger stick, and a compartment for carrying one or more packages of disposable items, typically including a test strip, a needle for the finger stick, and an alcohol swipe. The other half of the case includes a test strip reader, a user input device such as a key pad, and a display device such as a liquid crystal display. The meter reads a test strip carrying a biological sample, such as a droplet of blood, and within minutes displays test results, such as total cholesterol levels, on the meter's display.

The hand-held LIFESTREAM cholesterol meter drastically reduces the costs and inconvenience associated with obtaining cholesterol tests by performing total cholesterol tests in virtually any location, including a physician's office, a pharmacy, a clinic, or in the privacy of the patient's home. The meter produces the test results within minutes using on-board circuitry and programming. The meter also includes an on-board diagnostic program that prompts for additional diagnostic information, such as the patient's age, gender, weight, family history of heart disease, blood pressure, and so forth.

The meter then translates this diagnostic information, along with the test results, into diagnostic results that may be more meaningful to the user than the test results alone. For example, the meter may use a well-known methodology, such as the Framingham Medical Study, to produce diagnostic results including the user's cardiac age (as compared to chronological age), recommended weight loss, 5-year risk of heart attack, 10-year risk of heart attack, an assessment of stroke risk, and other results that will be easily and immediately understood by the patient. Like the test results themselves, these more meaningful diagnostic results are displayed on the meter within minutes.

Producing diagnostic results like "cardiac age" and "5-year risk of heart attack" rather than total cholesterol levels alone may motivate more people to change their lifestyles and reduce their cholesterol levels. Moreover, producing these diagnostic results instantaneously, inexpensively, and in a convenient location encourages frequent testing and provides patients with the positive feedback necessary to encourage continued compliance with drug therapies and lifestyle changes. Ultimately, widespread use of the LIFESTREAM cholesterol meter can be expected to improve cardiac health nationwide, shift the focus of cardiac treatment from corrective to preventative, improve the cardiac health of the population in general, and reduce medical costs and health insurance rates.

The benefits of the LIFESTREAM cholesterol meter may be improved over time and extended to other health problems because the meter is programmable and configured to perform multiple types of tests. That is, although the meter will be initially configured to perform total cholesterol tests using test strips and human blood samples, it is also configured to perform multiple types of tests using different types of test strips or other test media carrying other types of biological fluid or tissue samples. For example, the meter may also produce other types of blood lipid test results, such as HDL cholesterol, triglycerides, LDL cholesterol, etc. The meter may also perform other types of tests, such as blood glucose tests, AIDS tests, cancer tests, and virtually any other type of test that can be performed using a test strip or another suitable test medium carrying a sample of biological fluid or tissue. To accommodate multiple tests, the meter typically includes four romkey sockets that allow the meter to carry and read four different romkeys.

The LIFESTREAM cholesterol meter also works in connection with a network-based comprehensive health analysis and reporting system. The meter includes a data drive that writes patient data stored within the meter to a patient-held data storage device, such as a smartcard. This patient data typically includes patient identification information, the test results, the diagnostic information, and the diagnostic results. A computer station, such as a typical desktop or laptop personal computer, can then read the smartcard and establish a network connection with a health report server, typically over the Internet. The computer then downloads the patient data to the health report server, which prepares a comprehensive health report. This report is then transmitted back to the computer station, where it is printed out and delivered to the patient.

The health report server typically works in concert with the patient's physician or pharmacist, who may provide additional diagnostic information to the server, such as a newly-prescribed drug therapy, other currently-prescribed drugs for the patient, exercise and dietary recommendations, and so forth. Within minutes, the health report server assembles a comprehensive health report including a data sheet for the newly-prescribed drug, cross-reaction information for the newly-prescribed drug and the other currently-prescribed drugs, weight and total cholesterol goals, exercise and dietary recommendations, any food or activity warnings associated with the overall therapy package, and recommendations for on-going monitoring using the meter. This provides a complete written record of the patient's current condition, the therapy prescribed by the physician and filled by the pharmacist, and a roadmap for monitoring the patient's progress during the ensuing therapy.

The comprehensive health report may also include additional patient-specific information, such as the diagnostic information and results compiled by the meter, and additional diagnostic and health assessment information compiled by the server. For example, the report may include a trend analysis showing how cholesterol, blood glucose, and weight levels have changed over multiple readings. The report may also include generally-applicable educational information, such as coronary risk factors, dietary guidelines for reducing cholesterol levels, diabetes information, cancer information, and the like. At present, a patient may have to undergo a physical examination, pay thousands of dollars, and wait weeks to obtain a similar comprehensive health report. The network-based comprehensive health analysis and reporting system, working in concert with the LIFESTREAM cholesterol meter, allows the patient to obtain the report within minutes at a fraction of the cost.

The meter also includes a number of advantageous security features. For example, the meter cannot be activated until a user enters a proper activation code. This typically requires that the user call the manufacturer, which provides an opportunity to verify the meter's authenticity, set up a data file for the meter in the health report server, and tell the user how to update the meter software, if necessary. If a software update is indicated, the user may be instructed to activate the meter, initialize a smartcard, load the smartcard into a computer station, and establish a network connection with the health report server. The server can then download the new software (e.g., new version of an existing software module or a new software module) to the smartcard, which, in turn, can be placed back in the meter. The new software can then be uploaded to the meter.

The meter may also require validation of all test strips. Validation is important for some types of tests because readings obtained from each test strip will have to be interpreted correctly to obtain correct test results, and the calibration data used to interpret the readings from different lots of test strips may vary significantly. To allow proper calibration, each lot of test strips has a corresponding memory device, such as a romkey, that must be placed into the meter. The romkey includes a code number, an expiration date, and the calibration data for interpreting readings from the corresponding test strips. A test strip identification number that is mathematically derived from the code number is printed on the test strips or their packaging. The user must enter the proper test strip identification number into the meter, which the meter verifies with reference to the code number and the expiration date read from the romkey. This allows the meter to prevent the use of expired test strips and to also prevent test strips from being used in combination with incorrect romkeys.

Test strip validation is also an important aspect of one business model for deploying the meters. That is, the meters themselves may be provided for use at little or no charge to individual patients, whereas proprietary test strips will be sold to generate revenue from use of the meter. This may be a desirable business model for deploying the devices because it minimizes the initial cost that an individual patient must pay to begin using the device. Having to sell each device at its full cost, on the other hand, would undermine the economic feasibility of using the device in many contexts. For this business model, the meter should only activate for use with proprietary test strips after validation of the test strips.

The meter may also require each smartcard to be initialized with a personal identification number (PIN). Patient-specific PINs allow multiple patients to use the same meter, and also allows each patient's data to be secure to that patient. That is, only the patient or someone authorized by the patient (i.e., knowing the patient's PIN) can read the medical data stored on the smartcard. In this manner, each patient controls his or her own medical data, which can be a particularly important attribute for highly sensitive medical data, such as AIDS tests, cancer tests, and the like.

Generally described, the invention provides a test strip for use with a health monitoring device or meter. The test strip, when carrying a sample of biological fluid or tissue, may be read by the meter to obtain test results based on the sample and calibration data specific to the test strip. The test strip also corresponds to a memory device that stores a code number and the calibration data, which may also be read by the meter. The test strip has an associated test strip identification number that is mathematically derived from the code number and printed on the test strips, the packaging for the test strips, or a tag packaged with the test strips.

To verify test strips, the meter reads the code number from the memory device, mathematically derives a test strip identification number corresponding to the code number, compares the received test strip identification number to the derived test strip identification number, and activates the meter for use with the test strip only if the received test strip identification number corresponds to the derived test strip identification number.

The memory device may also store an expiration date for the test strip, which may be read by the meter. In this case, the meter may activate for use with the test strip only if the expiration date is prior to a current date read by the meter from an internal clock. The memory device may be a romkey that is inserted into a socket housed within the meter. The romkey is typically packaged with an associated group of the test strips, and the test strip identification number is typically printed on the test strips, printed on packaging for the test strips, or printed on a tag packaged with the test strip.

The invention also provides a hand-held health monitoring device or meter that includes an enclosure for housing a disposable test strip for use with the meter. The meter also includes a holder for removably supporting a device for gathering a sample of biological fluid or tissue, such as a finger stick. The meter also includes a test strip reader operable for reading the test strip carrying the sample of biological fluid or tissue and obtaining test results based on the sample and calibration data specific to the test strip. A memory reading device (e.g., romkey socket) functionally connected to the test strip reader reads the calibration data from a memory device (e.g., romkey). A user input device, such as a key pad, receives user input commands and a display device, such as a liquid crystal display, displays information on the meter.

The meter also includes a processor that is functionally connected to the test strip reader, the user input device, and the display device. The processor contains a program module that obtains the test results from the test strip reader and causes the display device to display the test results. A data drive functionally connected to the processor writes the test results to a removable memory storage device, such as a smartcard. The meter may be packaged in a clam-shell case that opens to reveal first and second compartments. The first compartment may contain the enclosure for housing the disposable test strip and the holder for removably supporting the biological fluid or tissue gathering device, and the second compartment may contain the test strip reader, the memory reading device, the display device, the processor, and the data drive.

To provide activation verification, the meter may receive an activation code through the user input device, compute an activation code based on the current date and instructions contained in an activation routine stored within the meter, and activate the meter only if the computed activation code corresponds to the received activation code. In addition, to provide security to a patient's medical data, the meter may determine whether a PIN has been previously stored on the removable memory storage device. If a PIN has not been previously stored on the removable memory storage device, the meter prompts the user to enter a PIN and stores the received PIN on the removable memory storage device. Alternatively, if a PIN has been previously stored on the removable memory storage device, the meter prompts the user to enter a PIN, compares the stored PIN to the received PIN, and writes the test results to the removable memory storage device only if the stored PIN corresponds to the received PIN.

The test strip reader may also be operable for reading a second type of test strip carrying a second sample of biological fluid or tissue and obtaining health-related test results based on the second sample of biological tissue or fluid and calibration data specific to the second type of test strip. In this case, the meter may include a second memory reading device (e.g., romkey socket) functionally connected to the test strip reader and operable for reading calibration data from a second memory device (e.g., romkey) corresponding to the second type of test strip. For example, the meter may read both blood lipid test strips and blood glucose test strips. As noted previously, the meter typically includes four romkey sockets that allow the meter to carry and read four different romkeys.

The meter may also prompt the user to enter diagnostic information using the user input device, such as gender, ethnicity, family history of heart disease, personal history of heart disease, personal history of diabetes, personal history of smoking, height, weight, age, blood pressure, and fitness level. The meter may then perform a diagnostic analysis and produce diagnostic results based on the test results and diagnostic information, and display diagnostic results. For example, the diagnostic results may include a medical risk index, a recommended weight loss, a five-year risk of heart attack, a ten-year risk of heart attack, a cardiac age, an extended age, and a risk of stroke.

The invention also provides a system for remotely producing health reports. This system includes a health monitoring device or meter, as described above, a computer station, and a health report server connected with the computer station through a network, such as the Internet. The meter writes health-related test results to a memory storage device. The computer station reads the test results from the memory storage device, establishes a network connection with the health report server, receives additional diagnostic information from a user, and transmits the test results and the additional diagnostic information to the health report server. The server, in turn, compiles a health report based on the test results and the additional diagnostic information and transmits the health report to the computer station, where the report may be printed and delivered to the patient.

The health report may include a trend analysis with test results compiled for a number of samples, such as total cholesterol level and blood glucose level trend reports. The additional diagnostic information may include a newly-prescribed drug and other currently-prescribed drugs, and the health report may include a data sheet for the newly-prescribed drug and information relating to cross-reactions between the newly-prescribed drug and the other currently-prescribed drugs. The health report may also include a target weight and total cholesterol levels, a schedule for future testing using the meter, health assessment summary, a coronary risk assessment, dietary guidelines to lower cholesterol, and other educational information.

The business model described above is largely dependent on the sale of proprietary test strips for the collection of revenue from end users. That is, the health monitoring device itself may be made available to individual patients at little or no cost, with the sale of proprietary test strips providing a major source of revenue for the proprietor of the health monitoring device. As noted previously, this may be a desirable business model for deploying the devices because it minimizes the initial cost that an individual patient must pay to begin using the device. Having to sell each device at its full cost, on the other hand, would undermine the economic feasibility of using the device in many contexts.

Nevertheless, it may also be desirable to provide a health monitoring device that does not rely on the sale of proprietary test strips as a major source of revenue. For example, the health monitoring device may be adapted to read non-proprietary test strips, or may incorporate a reusable and/or non-invasive testing device, such as an electrode, blood pressure monitoring device, sonic testing device, thermometer, saliva testing device, optical testing device, and the like. Of course, a non-invasive multi-use testing device may be used many times without affording the proprietor of the health monitoring device an opportunity collect revenue associated with each use of the device.

To provide an opportunity for the proprietor of the health monitoring device to collect revenue based on use of the device, the removable memory storage device may be utilized as a type of "debit card" or payment source for use with the health monitoring device. That is, the removable memory storage device may be purchased with a monetary value, or it may have a monetary value that is replenishable over the Internet using a bank credit or debit card or other conventional payment source. The health monitoring device may then deduct the cost of performing particular services from the monetary value represented by the monetary balance stored on the removable memory storage device. In other words, the health monitoring device may be configured to activate for the performance of a service upon deducting a charge for the service from a monetary value stored on a removable memory storage device inserted into the device.

This business model includes a health monitoring device operable for obtaining medical data associated with a patient and reading an initial monetary balance stored on a removable memory storage device. The health monitoring device determines whether the initial monetary balance is sufficient to pay a monetary value assigned to performance of a test involving the medical data to be performed by the testing device. If the initial monetary balance is sufficient to pay for the test, the health monitoring device computes a revised monetary balance by deducting the monetary value assigned to performance of the test from the initial monetary balance, replaces the initial monetary balance with the revised monetary balance on the removable memory storage device, and activates the health monitoring device for performance of the specified service.

The business model also includes a system that includes one or more of the health monitoring devices described above, one or more removable memory storage devices, and a network-based server operable for remotely charging a cost to a payment source and crediting the cost to an initial balance stored on the removable memory storage device. The network-based server may also remotely store the monetary value assigned to performance of the test on the removable memory storage device. In this case, the health monitoring device reads the monetary value assigned to performance of the test from the removable memory storage device. Thus, rate schedules for various services to be performed by the health monitoring device may be changed from time to time, based on quantity discounts or other considerations.

The invention also includes a secure medical records maintenance system. Although this system is specifically adapted for use with the health monitoring device described above, it may be used to store any type of electronic data including a wide variety of medical records, and is particularly convenient for storing a wide range of electronic medical data generated remotely from the hospital or doctor's office environment. The secure medical records maintenance system includes a number of removable memory storage devices, which are each operable for storing medical data for an associated patient. Each removable memory storage device also stores a patient-specified personal identification number (PIN), a medical records identification number secured by the PIN, and a patient identification number secured by the PIN.

The data stored on the removable memory storage device is downloadable to a two-server system including a first remote server that stores patient identification information indexed by patient identification numbers, and a second remote server that stores patient medical data indexed by the medical records identification number. For security purposes, the medical data maintained in the second remote server cannot be correlated to the associated patient identification information maintained in the first remote server based on the information contained in the first and second remote servers.

To allow correlation of the data stored in the two servers, the secure medical records maintenance system includes a correlation table uniquely associating each medical records identification number with a particular one of the patient identification numbers. The correlation table for a particular patient typically resides on the patient's removable memory storage device. The correlation table for a practitioner's patients may also reside on the practitioner's computer, such as a doctor's or pharmacist's computer, that is associated with a licensed medical practitioner having an assigned professional registration number. For further security, the first and second remote servers are accessed by the practitioner's computer through encrypted communications secured by an application procedure that includes validation of the practitioner's registration number. The application procedure may be further secured by receipt and validation of a practitioner-supplied PIN. Moreover, the application procedure typically includes issuance of a client certificate insuring that access to the first and second remote servers occurs from the same practitioner's computer and browser that initiated the application procedure.

Because the data on the servers is separate and secure from each other, access may be granted to either server without identifying any particular patient's medical data. For example, access may be granted to the first remote server, but not to the second server, for the purpose of generating a mailing list of patients without divulging any medical data associated with the patients. Similarly, access may be granted to the second remote server, but not to the first server, for the purpose of conducting investigative analyses involving the medical data without divulging any patient identification information associated with the patients.

For further data security and because each removable memory storage device only has a limited data storage capability, the medical data stored on each removable memory storage device may be automatically erased from the memory storage device after the data is entered into the second remote server. To obtain the medical data, the removable memory storage device is receivable within a hand-held health monitoring device operable for storing the medical data on the removable memory storage device. And to download the medical data to the medical records maintenance system, the removable memory storage device is receivable within a computer operable for reading the medical data and transmitting it to the second remote server over the Internet.

That the invention improves over the drawbacks of health monitoring and diagnostic systems and accomplishes the advantages described above will become apparent from the following detailed description of the exemplary embodiments and the appended drawings and claims.

BRIEF DESCRIPTION OF THE DRAWINGS

FIG. 22 is an illustration of a "billing information" user interface in a secure medical records maintenance system.

FIG. 23 is an illustration of a "cover letter" user interface in a secure medical records maintenance system.

FIG. 25 is an illustration of a "patient information" user interface in a secure medical records maintenance system.

FIG. 26 is an illustration of a "questionnaire data" user interface in a secure medical records maintenance system.

FIG. 28 is an illustration of typical health assessment charts generated by a secure medical records maintenance system.

DETAILED DESCRIPTION OF EMBODIMENTS OF THE INVENTION

Hand-Held Health Monitoring and Diagnostic Device

Figure 1A:
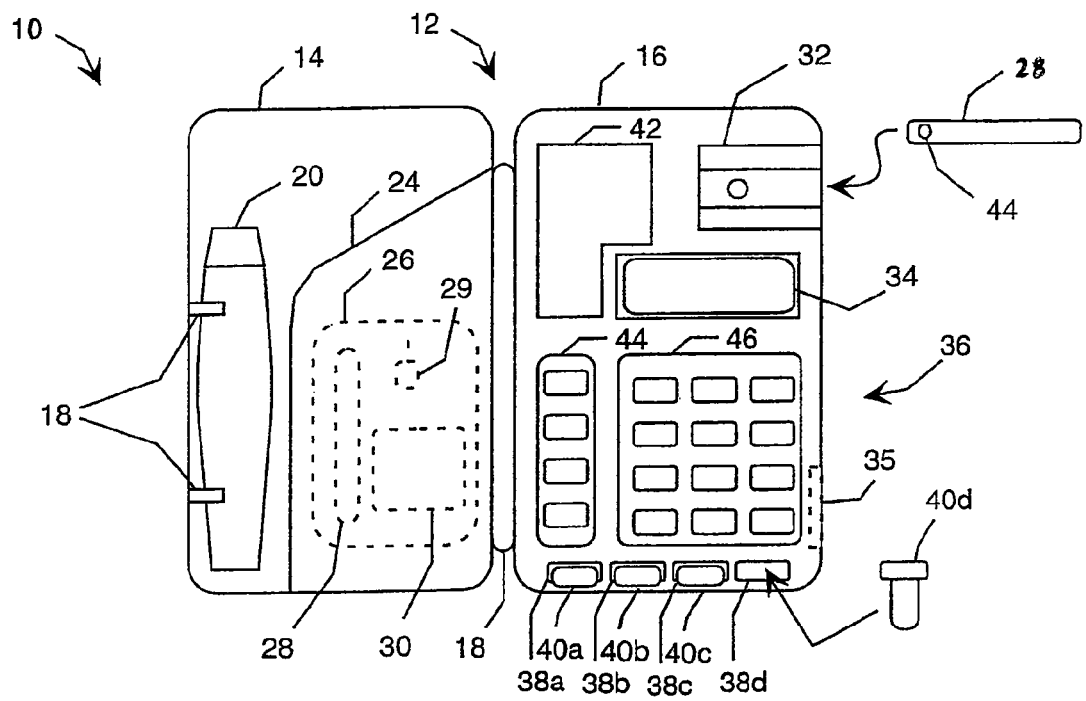
FIG. 1A is a front view of a hand-held health monitoring and diagnostic device in an open position.

Turning now to the figures, in which like numerals refer to like elements through the several figures, FIG. 1A is a front view of a hand-held health monitoring and diagnostic device 10, which is also referred to as a meter or a LIFESTREAM cholesterol meter. The meter 10 is housed in a clam-shell case 12 including a first compartment 14 and a second compartment 16. The case 12 may be opened, as shown in FIG. 1A, or closed about a hinge 18. This allows a patient to close the meter 10 for transportation or storage, and then easily open it for use. When in use, the patient may place the meter 10 in the open position on a flat surface, such as a table or seat, or hold the meter by hand.

Although the meter 10 is shown in a hinged clam-shell, hand-held configuration, it could alternatively be embodied in other configurations, such wall-mounted, built into a movable cart, built into a desktop computer, built into a fixed podium, and so forth. In addition, the hinged clam-shell case could be replaced by a non-hinged case, a separable multi-piece case, a case with a pull-out drawer, a case with a flat cover, a meter that fits into a separate zippered case, and other types of single- or multi-piece configurations. Many other variations of the meter case configuration will be apparent to those skilled in the art.

The first compartment 14 includes a holder 18 for removably supporting a biological sample gathering device, in this instance a conventional spring-loaded finger stick 20. Although the holder 18 is shown as a clip with two arms that fit snugly against the finger stick 20, the holder may have any other configuration suitable for removably supporting the finger stick, such as a channel into which a pencil-like finger stick is inserted, an openable enclosure, snaps, a VELCRO fastener, and the like. If samples other than blood are to be gathered, the first compartment 14 could alternatively house other types of biological sample gathering devices, such as a skin sample collector, a saliva collector, a stool sample collector, and so forth. In addition, the meter 10 may include other types of instruments for gathering test data, for example the meter may be adapted to read non-proprietary test strips, or may incorporate a reusable and/or non-invasive testing device, such as an electrode, blood pressure monitoring device, sonic testing device, thermometer, saliva testing device, optical testing device, and the like.

The first compartment 14 also includes an openable enclosure 24 for storing one or more packages 26 of disposable items. Specifically, each package may contain a test strip 28, a needle 29 for the finger stick 20, and an alcohol swipe 30. These disposable items are tailored for one-time use with the finger stick 20. If the meter 10 includes biological sample gathering devices other than the finger stick 20, other types of disposable items may be stored in the enclosure 24. In addition, the enclosure 24 may have other configurations suitable for storing or holding disposable items, such as a drawer, a tilting channel, a clip, and so forth.

The second compartment 16 houses the electronic components of the meter 10, including a test strip reader 32, a display device 34, a user input device 36, and one or more memory reading devices 38a-d. Each of these memory reading devices is configured to receive a corresponding memory device 40a-d. The second compartment 16 also includes an instructional label 42 located adjacent to the display device 34. Internally, the second compartment 16 houses a motherboard, an analyzer board, and a data drive that control the functionality of the meter 10. These internal components are described with reference to FIG. 3, and the functionality of the meter 10 is described with reference to FIGS. 4-13. Additional functionality of the meter 10 for use with a debit-card type payment system is described with reference to FIGS. 30-31.

The test strip reader 32 may be a GLUCOTREND Basic TIM (test instrument module) assembly No. 1739905-741 manufactured by. Boehringer Mannheim, Roche Diagnostics GmbH. This is a commercially-available optical test strip reader suitable for reading chemical test strips carrying human blood samples and producing either blood glucose readings, total cholesterol readings, or both. Alternatively, other suitable types of test strip readers may be included in the meter 10, and multiple test strip readers may be included in the meter, if appropriate. This may be desirable, for instance, if biological samples other than blood are to be analyzed by the meter. The meter 10 may be configured with additional reusable and/or non-invasive testing devices, such as an electrode, blood pressure monitoring device, sonic testing device, thermometer, saliva testing device, optical testing device, and the like.

The display device 34 may be a conventional liquid crystal display (LCD) configured to display at least two lines of text including at least 14 characters per line. This visual display works in concert with a speaker 35 that beeps to convey audible messages. The speaker may also produce other types of audible messages, such as tones, recorded messages, a simulated human voice, and the like. The meter 10 may also include other types of visual display devices, such as an electronic capacitive matrix, a small video display, or other types of suitable visual display devices. The meter 10 may also include a jack for connecting the meter to external display devices, such as a computer monitor or video display.

The user input device 36 may be a keypad with a first key section 44 and a second key section 46. The first key section 44 includes four keys, a "scroll" key, a "yes" key, a "no" key and an "enter" key. The second key section 46 includes twelve keys, including ten numerical keys, a "clear" key, and an "on/off" key. The user input device 36 may include other key patterns and other types of user input devices, such as a touch-sensitive screen, a voice-recognition device, or other input devices. The meter 10 may also include a jack for connecting the meter to external input devices, such as a keyboard or joystick.

The memory reading devices 38a-d may be romkey sockets, and the memory devices 40a-d may be romkeys that removably insert into the sockets. As shown in FIG. 1A, the meter 10 preferably includes four romkey sockets. Nevertheless, the meter 10 could also be configured with only one socket because the romkeys themselves are removable. The romkeys, which store identification, expiration, and calibration data for a corresponding lot of test strips 28, are desirable because they are small, may be easily packaged with the corresponding test strips, and have an adequate amount of computer-readable memory. But the romkey sockets may be replaced by a magnetic card reader, an optical reader, or another reader suitable for use with a memory storage device that can be easily shipped with a corresponding lot of test strips 28 and has an adequate amount of computer-readable memory.

The instructional label 42 located adjacent to the display device 34 typically includes instructions for entering diagnostic information into the meter 10. This label may also include instructions for using the meter 10 in concert with a remote health report system, which is described with reference to FIG. 2. As this type of information may be understood best when explained by a physician or pharmacist, the instructional label 42 may be included on meters provided to physicians and pharmacists, but may be excluded from meters provided for home use by individual patients. The programmed functionality of the meter may also be adjusted accordingly.

To use the meter 10, a patient first opens the meter and removes the finger stick 20 and the package of disposable items 26. The patient then opens the package, installs the needle 29 in the finger stick 20, and wipes the alcohol swipe 30 on the area of the finger to be stuck with the needle. The patient also inserts the correct romkey for the test strip 28, represented by the romkey 40d, into a corresponding romkey socket 38d and manipulates the keypad 44, 46 to indicate to the meter 10 which romkey socket contains the correct romkey. The patient then sticks the selected finger with the finger stick 20, places a droplet of blood 44 on an indicated area of the test strip 28, and inserts the test strip 28 into the test strip reader 32.

The user then manipulates the input device 36 by following prompts displayed on the display device 34 to complete the test. Within minutes, the meter 10 completes the test and displays the test results, such as total cholesterol levels, blood glucose levels or another testing service provided by the meter, on the display device 34. If appropriate, the user may also manipulate the input device 36 to enter additional diagnostic information into the meter, such as gender, ethnicity, family history of heart disease, personal history of heart disease, personal history of diabetes, personal history of smoking, height, weight, age, blood pressure, and fitness level. Within minutes, the meter 10 performs a diagnostic analysis and produces diagnostic results, such as a medical risk index, a recommended weight loss, a five-year risk of heart attack, a ten-year risk of heart attack, a cardiac age, an extended age, and a risk of stroke. These diagnostic results are also immediately displayed on the display device 34.

For a blood lipid or cholesterol test, the well-known Framingham Medical Study may provide the methodology used by the meter 10 to produce the diagnostic results from the test results and the diagnostic information. Other methodologies, such as those sanctioned by the National Cholesterol Education Program, the American Heart Association, the American Medical Association, or another appropriate organization may also be used. In fact, the meter 10 may allow the user to select among several alternative diagnostic program modules stored within the meter. These diagnostic program modules may be updated from time to time, and new diagnostic program modules may be added to the meter 10 through the data drive, which is described below.

Figure 1B:
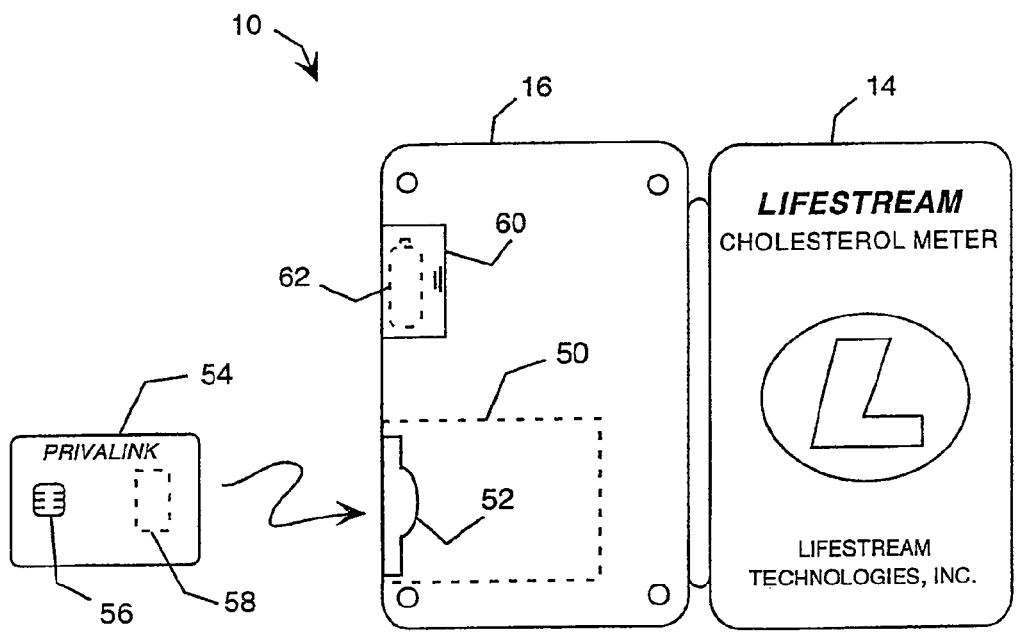
FIG. 1B is a rear view of the hand-held health monitoring and diagnostic device of FIG. 1 in an open position.

FIG. 1B is a rear view of the meter 10, which shows the outside of the meter. The outside of the first compartment 14 includes the manufacturer's name, Lifestream Technologies, Inc., and the meter's trademark, LIFESTREAM. The outside of the second compartment 16 includes a data drive 50, which includes an opening 52 for receiving a removable memory storage device 54. For example, the data drive 50 may be a smartcard drive, such as an STM IC: MC33560ADW manufactured by Motorola, and the removable memory storage device 54 may be a smartcard usable with this drive. This smartcard typically includes an electrical contact 56 for reading and writing data and a small microprocessor 58, which typically controls security aspects of the smartcard. Specifically, the smartcard includes a PIN-protected secure memory and an unsecure memory. The microprocessor 58 controls the PIN and any other functionality resident on the smartcard.

The smartcard is an advantageous memory storage device because of its small size, its on-card PIN security feature, and its on-board programmable processing unit. Moreover, it is expected that smartcards will become increasingly popular in the near future, and most personal computers will come with factory-installed smartcard drives. Nevertheless, the meter 110 could include other types of data drives, such as a floppy disk drive, an optical disk drive, a removable RAM chip, or any other suitable type of removable memory storage device. Furthermore, the meter 10 could also include a wire-line data port for connecting a cable or another computer station in addition to or as an alternative to the data drive. Similarly, the wire-line data port could be replaced by a wireless communication device, such as a radio-frequency link, a laser link, an infra-red link, and so forth.

The second compartment 16 also includes a battery enclosure 60 housing a removable battery 62 for powering the meter 10. The battery 60, which may be a disposable 9 Volt battery, may be replaced or augmented by an A/C power cord and an appropriate power inverter. The battery 60 also be replaced by a rechargeable battery augmented with a battery charger that may be located within the meter 10 or in a separate enclosure, such as a storage container for housing the meter when it is not in use.

Remote Health Report System

Figure 2:
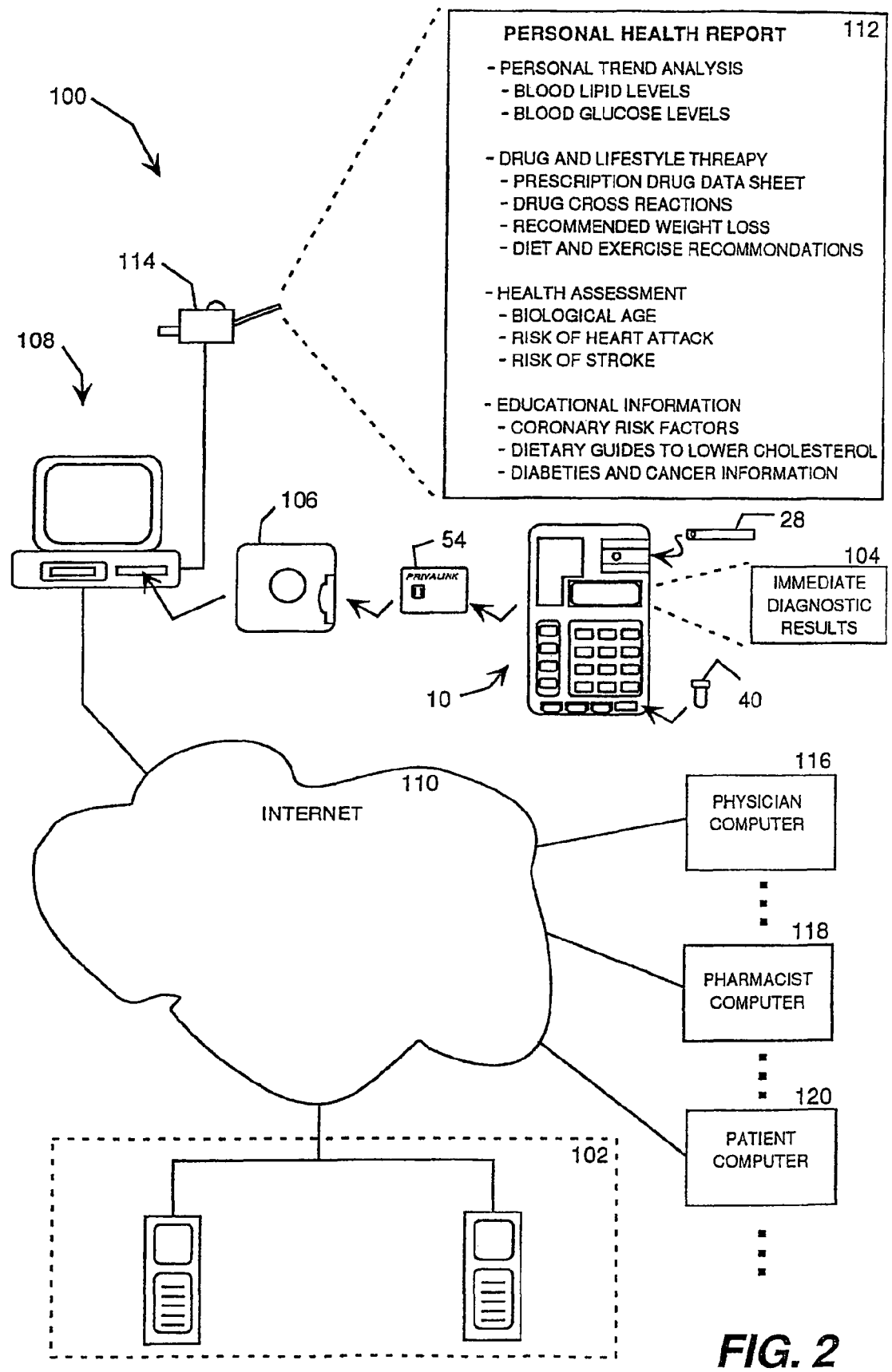
FIG. 2 is a block diagram illustrating a system for remotely producing health reports.

FIG. 2 is a block diagram illustrating a system 100 for remotely producing health reports. The PIN-securable smartcard described above allows multiple patients to use the same meter, and also allows each patient to control access to his or her medical data. The smartcard is typically used as a temporary storage location for one or several test results. From time to time, each patient is expected to download the medical data contained on his or her smartcard to a health report server 102 for permanent storage. The smartcard is then erased (except for the PIN and any other security information contained in the secure memory), which frees the memory space for new medical data. The smartcard may also be used to receive new program modules or new versions of program modules from the health report server 102 and upload these program modules to the meter 10.

The system 100 includes the meter 10, which downloads medical data to the removable memory storage device 54. This medical data typically includes patient identification information, test results generated by the meter, diagnostic information entered into the meter 10 by the patient, and the diagnostic results 104 computed by the meter and immediately displayed on the meter at the time of the test. If the removable memory storage device 54 is a smartcard, it may then be placed in a converter, such as a conventional smartcard-to-floppy-disk converter 106, which can be directly inserted into a computer station 108. The converter 106 will be unnecessary, of course, if the computer station 108 includes a smartcard drive, or if another communication mechanism is employed to transmit information between the computer station 108 and the meter 10.

Once the medical data arrives at the computer station 108, it establishes a network connection with the health report server 102, typically over the Internet 110. The medical data is then transmitted to the health report server 102, which may also prompt the user for additional diagnostic and health report information. Specifically, the health report server 102 typically works in concert with the patient's physician or pharmacist, who may provide additional diagnostic information to the server, such as a newly-prescribed drug therapy, other currently-prescribed drugs for the patient, exercise and dietary recommendations, and so forth. Within minutes, the health report server 102 assembles a comprehensive health report 112 that is transmitted back to the computer station 108, where it may be printed on a local printer 114. User access procedures and a menu-driven user interface system for generating the health reports is described with reference to FIGS. 17-29.

The comprehensive health report 112 typically includes a data sheet for the newly-prescribed drug, cross-reaction information for the newly-prescribed drug and the other currently-prescribed drugs, weight and total cholesterol goals, exercise and dietary recommendations, any food or activity warnings associated with the overall therapy package, and recommendations for on-going monitoring using the meter. This provides a complete written record of the patient's current condition, the therapy prescribed by the physician and filled by the pharmacist, and a roadmap for monitoring the patient's progress during the ensuing therapy.

The comprehensive health report may also include additional patient-specific information, such as the diagnostic information and results compiled by the meter, and additional diagnostic and health assessment information compiled by the server. For example, the report may include a trend analysis showing how blood lipid, blood glucose, and weight levels have changed over multiple readings. The report may also include generally-applicable educational information, such as coronary risk factors, dietary guidelines for reducing cholesterol levels, diabeties information, cancer information, and the like. At present, a patient may have to undergo a physical examination, pay thousands of dollars, and wait weeks to obtain a similar comprehensive health report. The network-based comprehensive health analysis and reporting system, working in concert with the LIFESTREAM cholesterol meter, allows the patient to obtain the report within minutes at a fraction of the cost.

The Internet 10 allows a wide variety of users to access the health report server 102, which allows meters to be deployed in a variety of settings. For example, the accessing computer stations may include a physician's computer station 116, a pharmacist's computer station 118, an individual's computer station 120, and many others. This will allow meters to be effectively deployed for multi-patient use in clinics, physicians' offices and pharmacies, as well as for individual patient or family use in the privacy of their own homes.

Functional Operation of the Meter

Figure 3:
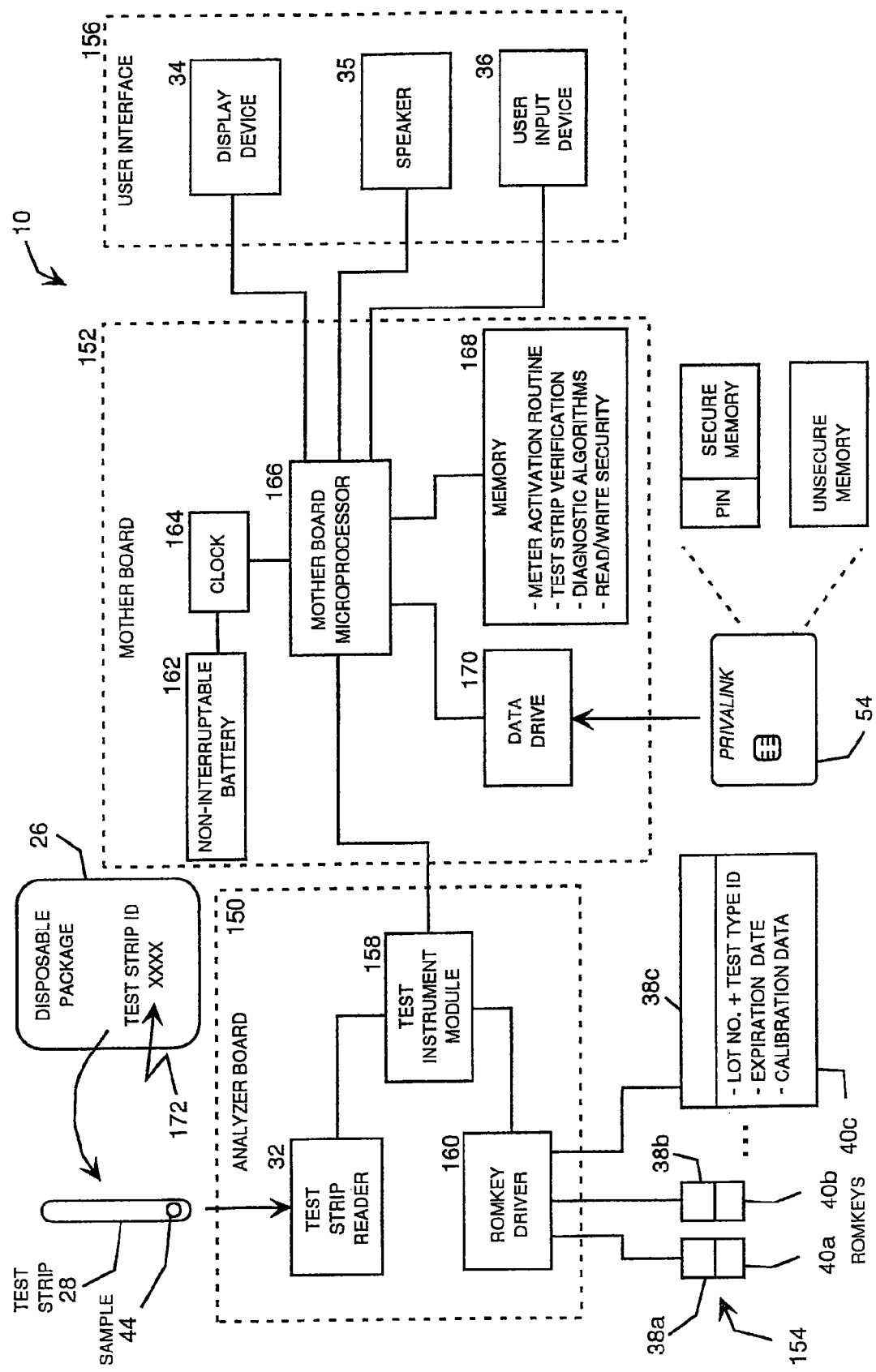
FIG. 3 is a functional block diagram of a health monitoring and diagnostic device.

FIG. 3 is a functional block diagram of the health monitoring and diagnostic device 10, which is also referred to as a meter. The meter includes an analyzer board 150, a mother board 152, a memory reading device 154 including the romkey sockets 38a-d and corresponding romkeys 40a-d, and a user interface 156 including the display device 34, the speaker 35, and the input device 36. The memory reading device 154 and the user interface 156 were described with reference to FIG. 1A. Although the analyzer board 150 and the mother board 152 may be configured as two separate integrated circuit boards, alternatively they may be combined into a single integrated circuit board, or deployed on more than two integrated circuit boards.

The analyzer board 150 may be part of the GLUCOTREND Basic TIM (test instrument module) assembly No. 1739905-741 manufactured by Boehringer Mannheim, Roche Diagnostics GmbH. This board includes the test strip reader 32, which was described with reference to FIG. 1A, a test instrument module 158, and a romkey driver 160. The test strip reader 32 reads the test strip 28 carrying the blood sample 44. The romkey driver 160 reads the calibration data for the test strip 28 from a corresponding romkey, such as the romkey 40d, and the test instrument module 158 computes the test results from the test strip reading and the calibration data. These test results are then passed to the motherboard 152.

The motherboard 152 includes a non-interruptible battery 162, such as a lithium battery. The non-interruptible battery 162, which powers the on-board clock 164, is distinct from the power supply battery 62 (shown on FIG. 1B). The additional non-interruptible battery 162 allows the clock to continue functioning even when the power supply battery 62 runs down or is removed from the meter 10. The motherboard 152 also includes a processor 166 and a memory 168 that control the functionality of the meter 10. Specifically, the memory 168 stores and the processor 166 implements a meter activation routine, test strip verification routine, diagnostic routines, and a read/write security routine. These program modules are described with reference to FIGS. 4-13. The motherboard 152 also includes a data drive 170 that reads data from and writes data to the removable data storage device 54, such as a smartcard.

The mother board processor 166 may be a 40-pin DIP CPU Model No. MC68HC705C9ACP manufactured by Motorola. The data drive 170 may be a STM IC Model No. MC33560ADW ISO read/control card manufactured by Motorola, supported by an ISO Card Socket, Model No. 145206-3 physical interface manufactured by AMP. However, any of these specific devices may be replaced by equivalent devices capable of performing the functionality of the meter 10 described in this specification.

To verify test strips, the romkey driver 160 reads a code number from a romkey, such as the romkey 40d, installed in the meter 10. The code number typically includes the lot number for the corresponding test strips and a test type ID stored on the romkey by the manufacturer of the meter 10. The test strip 28 has an associated test strip identification number 172 that is mathematically derived from the code number and printed on the test strip itself, the packaging for the test strip, or a tag packaged with the test strip. The meter 10 prompts the user to enter the test strip identification number 172 into the meter using the keypad 46.

The meter 10 also reads the code number from the memory device, mathematically derives a test strip identification number corresponding to the code number, compares the received test strip identification number to the derived test strip identification number, and activates the meter for use with the test strip only if the received test strip identification number corresponds to the derived test strip identification number. The romkey 40d also stores an expiration date for the corresponding test strip 28. The meter 10 reads the expiration date and activates for use with the test strip 28 and the romkey 40d only if the expiration date is prior to a current date read by the meter from the internal clock 164.

FIGS. 4-14 are logic flow diagrams illustrating examples of the functionality that may be implemented by the meter 10 and the system 100 for remotely generating health reports. The following description of these logic flow diagrams will also refer to the elements shown on FIGS. 2 and 3. It should be understood that these examples illustrate the use of these components in producing total cholesterol tests and related health reports. In particular, the specific diagnostic information gathered and the specific diagnostic results described are those associated with the well-known Framingham Medical Study, which is incorporated herein by reference. Although this particular program module illustrates the operation of an illustrative embodiment of the invention, those skilled in the art will understand that the meter 10 and the system 100 could be programmed with additional and different program modules.

In addition, as the meter 10 is configured with multiple romkey sockets and programmed to accept additional program modules in the future, it will be appreciated that similar functionality may be implemented in the future for blood glucose tests and diabetes-related health reports, AIDS tests and related health reports, cancer tests and related health reports, and so forth. Additional functionality of the meter 10 for use with a debit-card type payment system is described with reference to FIGS. 30-31.

Meter Activation

Figure 4:
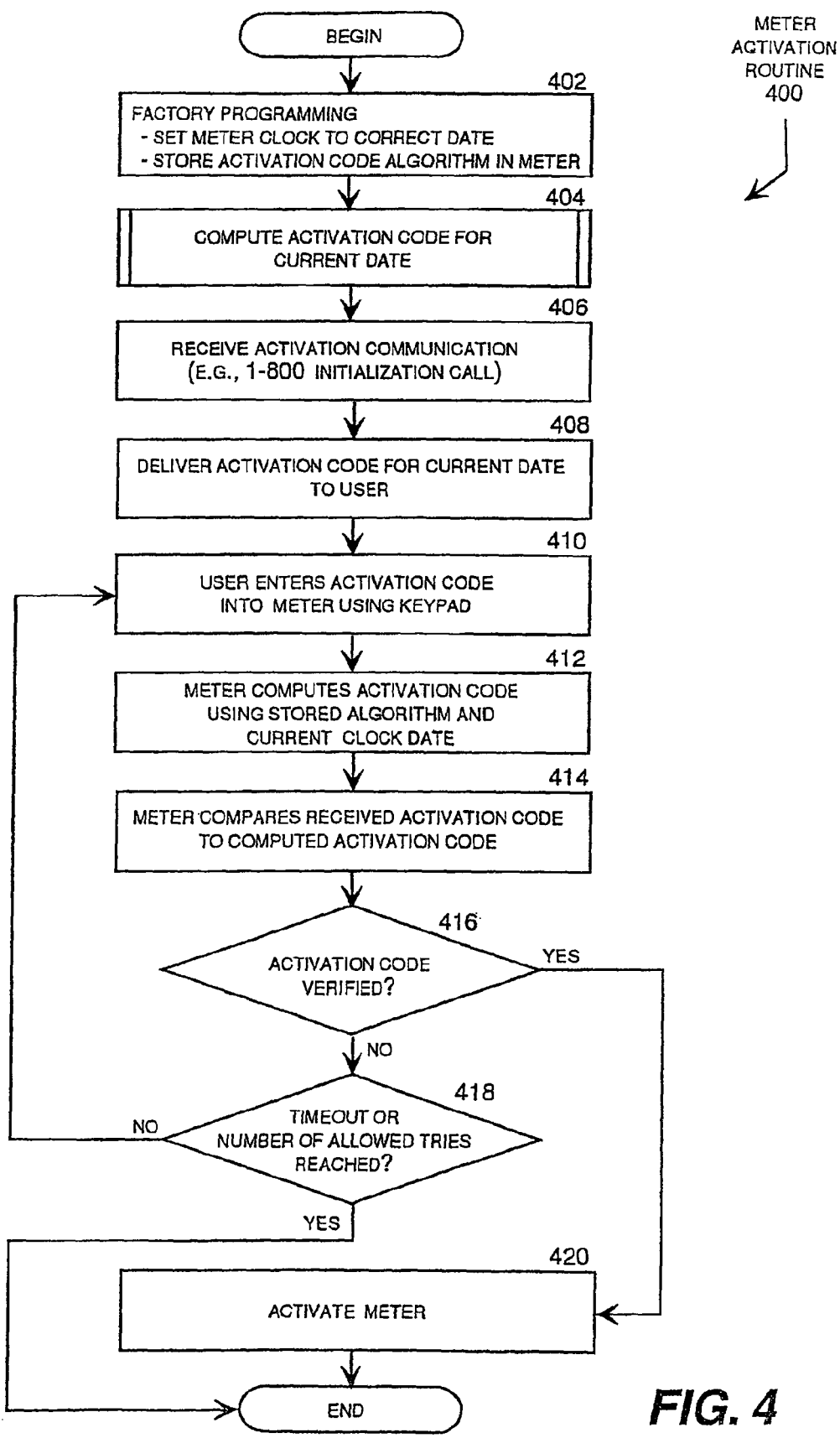
FIG. 4 is a logic flow diagram illustrating a routine for activating a health monitoring and diagnostic device.

FIG. 4 is a logic flow diagram illustrating a routine 400 for activating the meter 10. This routine requires that a user enter a proper activation code to activate the meter 10. This typically requires that the user call the manufacturer, which provides an opportunity to verify the meter's authenticity, set up a data file for the meter in the health report server, and tell the user how to update the meter software, if necessary. If a software update is indicated, the user may be instructed to activate the meter, initialize a smartcard, load the smartcard into a computer station, and establish a network connection with the health report server. The server can then download the new software (e.g., new version of an existing software module or a new software module) to the smartcard 54, which, in turn, can be placed back in the meter 10. The new software can then be uploaded to the meter.

In step 402, the meter 10 is programmed at the factory, by setting the internal clock 164 to the correct date and storing an activation code algorithm within the meter. Step 402 is followed by routine 404, in which the activation site, typically the manufacturer, computes an activation code for the current day. That is, each day-the activation site computes a new activation code that is valid only for that day. The activation code is computed using the same algorithm that was stored in the meter 10 in step 402. This algorithm is described below with reference to FIG. 5.

Step 404 is followed by routine 406, in which the activation site receives an activation communication for the purpose of activating a meter 10. The user of the meter typically places this communication by placing a telephone call to a telephone number (e.g., a "1-800" or other toll-free telephone number) on the meter or on the packaging or documentation provided with the meter. Step 406 is followed by routine 408, in which the activation site delivers. the activation code for the current date to the calling user. Step 408 is followed by routine 410, in which the calling user enters the activation code into the meter 10 by manipulating the user input device 36.

Step 410 is followed by step 412, in which the meter 10 verifies the received activation code by computing an activation code using its on-board activation code algorithm and the current date read from its internal clock 164. In doing so, the meter 10 uses the same algorithm that was used by the activation site to compute the activation code that was delivered to the user and entered into the meter (i.e., the algorithm described with reference to FIG. 5). Step 412 is followed by routine 414, in which the meter 10 compares the received activation code to the computed activation code. Step 414 is followed by routine 416, in which the meter 10 determines whether the activation is verified by determining whether the received activation corresponds to the computed activation code.

If the activation is not verified, the "NO" branch is followed from step 416 to step 418, in which the meter 10 determines whether a timeout condition or an allowed number of tries has been reached. If a timeout condition or an allowed number of tries has not been reached, the "NO" branch loops from step 418 to step 410, and the meter 10 displays an error and prompts the user to reenter the activation code. If a timeout condition or an allowed number of tries has been reached, the "YES" branch is followed from step 418 to the "END" step, and the meter 10 is not activated.

Referring again to step 416, if the activation is verified, the "YES" branch is followed from step 416 to step 420, in which the meter 10 is activated. Step 412 is followed by the "END" step, in this case with the meter 10 activated.

Figure 5:
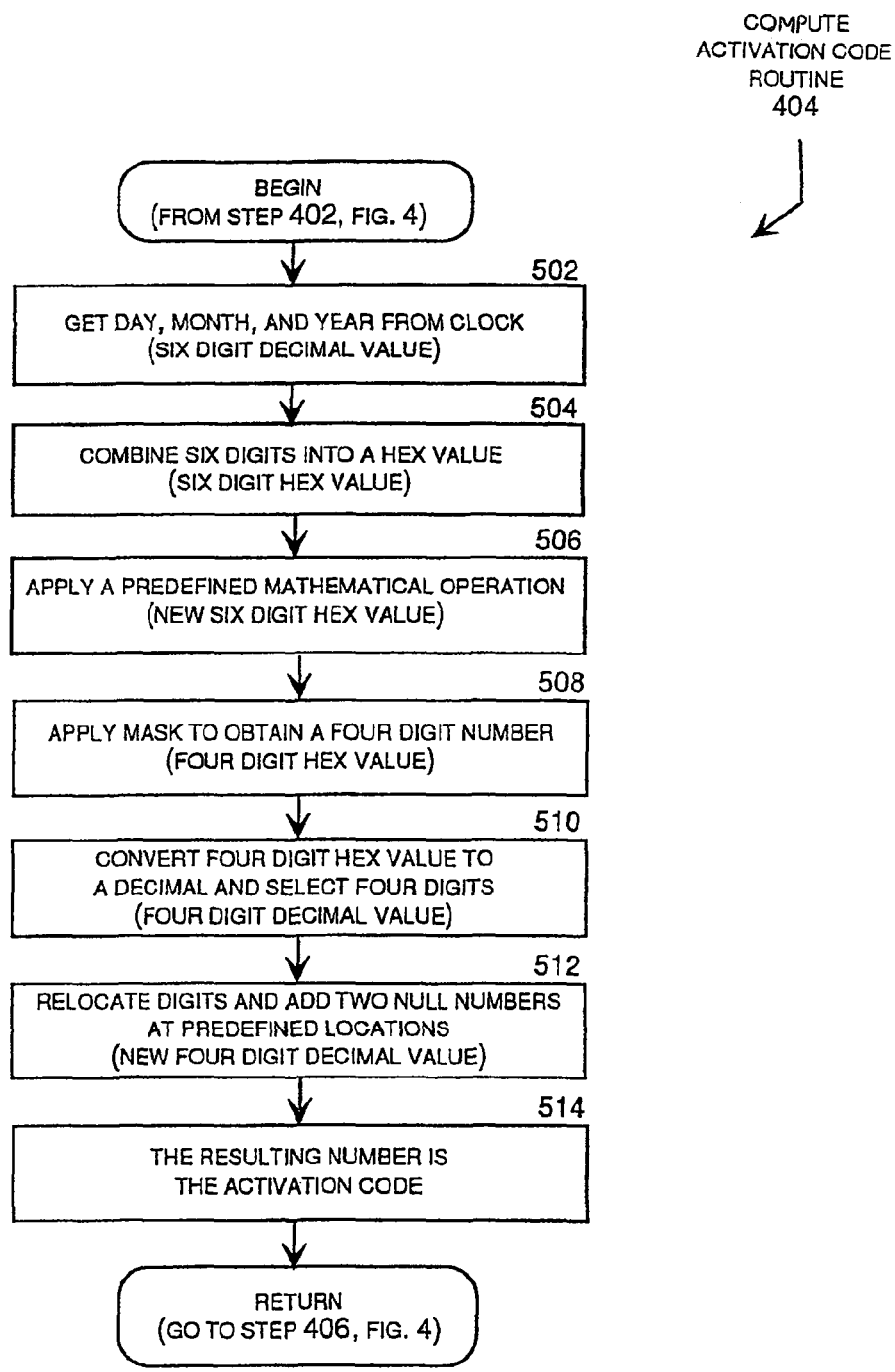
FIG. 5 is a logic flow diagram illustrating a routine for computing an activation code for a health monitoring and diagnostic device.

FIG. 5 is a logic flow diagram illustrating a routine 404 for computing an activation code for the meter 10 or the activation site, referred to collectively below as the "computing entity." Routine 404 begins following step 402 shown on FIG. 4. In step 502, the computing entity gets the day, month, and year (six digit decimal) from the internal clock 164. Step 502 is followed by step 504, in which the computing entity combines the six digits defining the date into a hex value (six digit hex). Step 504 is followed by step 506, in which the computing entity applies a predetermined mathematical operation to this hex value to compute a new hex value (new six digit hex).

Step 506 is followed by step 508, in which the computing entity applies a mask to the new six digit hex value to obtain a four digit hex value (new four digit hex). In other words, the computing entity selects a predetermined four of the six digits for further processing. Step 508 is followed by step 510, in which the computing entity converts this new four digit hex value to a decimal value (four digit decimal value). Step 510 is followed by step 512, in which the computing entity relocates one or more of the digits and adds one or more null numbers at predefined locations (new four digit decimal value). Step 512 is followed by step 514, in which the computing entity uses the resulting new four digit decimal number as the activation code. Step 514 is followed by the "RETURN" step, which goes to step 406 on FIG. 4.

The mathematical operation applied in step 506 may be any of a variety of algorithms designed to quasi-randomize the result. For example, the digits may be grouped into subsets that, in turn, are used in one or more linear mathematical operations, such as addition, subtraction, multiplication, division, raising to a power, raising to a fraction, and the like. For example, a polynomial formula may be applied to the digits or subsets of the digits. The digit shuffling operation applied in step 512 is also applied to quasi-randomize the result. Many other types of quasi-randomizing methodologies will be apparent to those skilled in the art.

Test Strip Validation

Figure 6:
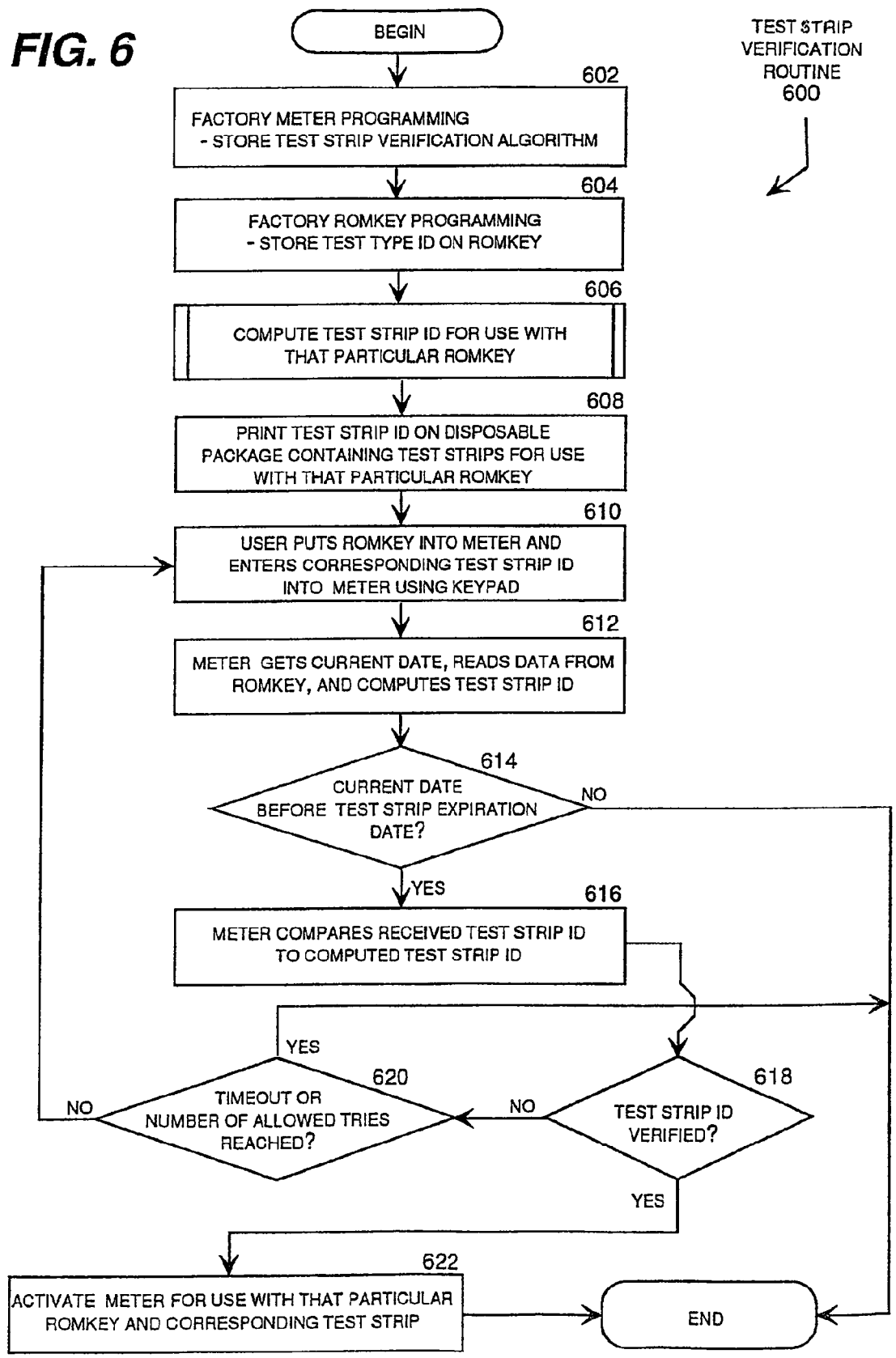
FIG. 6 is a logic flow diagram illustrating a routine for verifying a test strip for a health monitoring and diagnostic device.

FIG. 6 is a logic flow diagram illustrating a routine 600 for verifying a test strip for the meter 10. In step 602, the meter 10 is programmed at the factory with a test strip validation algorithm. Step 602 is followed by step 604, in which a romkey with a corresponding lot of test strips is programmed with a test type ID. This test type ID, together with a lot number for the test strips placed on the romkey by the test strip manufacturer, forms a four-digit code number that is resident on the romkey when it leaves the factory.

Step 604 is followed by routine 606, in which a test strip ID is mathematically derived from the romkey code number. Routine 606 is described below with reference to FIG. 7. Routine 606 is followed by step 608, in which the test strip ID is printed on the lot of test strips corresponding to the romkey, on the packaging for the test strips, or tags that are packaged with the test strips. The test strips are then packaged with corresponding romkeys and distributed for use with various meters. It should be understood that many identical romkeys may be produced for each lot of test strips because one romkey is included in each distribution-sized package, and a production-sized lot of test strips may be many times larger than a distribution-sized package.

Step 608 is followed by step 610, in which the user of a meter 10 puts a romkey into the meter and enters the corresponding test strip ID into the meter using the user input device 36. This is the test strip ID that was printed on the test strip, its packaging, or a tag packaged with the test strip in step 608. Step 610 is followed by step 612, in which the meter 10 gets the current date from the internal clock 164, reads the code number and expiration date from the romkey, and computes a test strip ID number based on the code number. The test strip ID number is derived from the code number using the same algorithm that was used to compute the test strip ID number at the factory in routine 606.

Step 612 is followed by step 614, in which the meter 10 determines whether the current date is prior to the expiration date read from the romkey. If the current date is not prior to the expiration date read from the romkey, the "NO" branch is followed to the "END" step, and the meter is not activated for use with the instant romkey. If the current date is prior to the expiration date read from the romkey, the "YES" branch is followed to step 616, in which the meter 10 compares the received test strip (input by the user) to the computed test strip ID (derived from the code number read from the romkey). Step 616 is followed by step 618, in which the meter 10 verifies the test strip if the received test strip corresponds to the computed test strip ID.

If the meter 10 verifies the test strip, the "YES" branch is followed from step 618 to step 622, in which the meter 10 activates for use with the instant test strip and romkey. Step 622 is followed by the "END" step. If the meter 10 does not verify the test strip, the "NO" branch is followed from step 618 to step 620, in which the meter 10 determines whether a timeout condition or an allowed number of tries has been reached. If a timeout condition or an allowed number of tries has not been reached, the "NO" branch loops from step 620 to step 610, and the meter 10 displays an error and prompts the user to reenter the test strip ID and/or insert the correct romkey. If a timeout condition or an allowed number of tries has been reached, the "YES" branch is followed from step 620 to the "END" step, and the meter 10 is not activated for the instant test strip and romkey.

Test Strip ID Assignment

Figure 7:
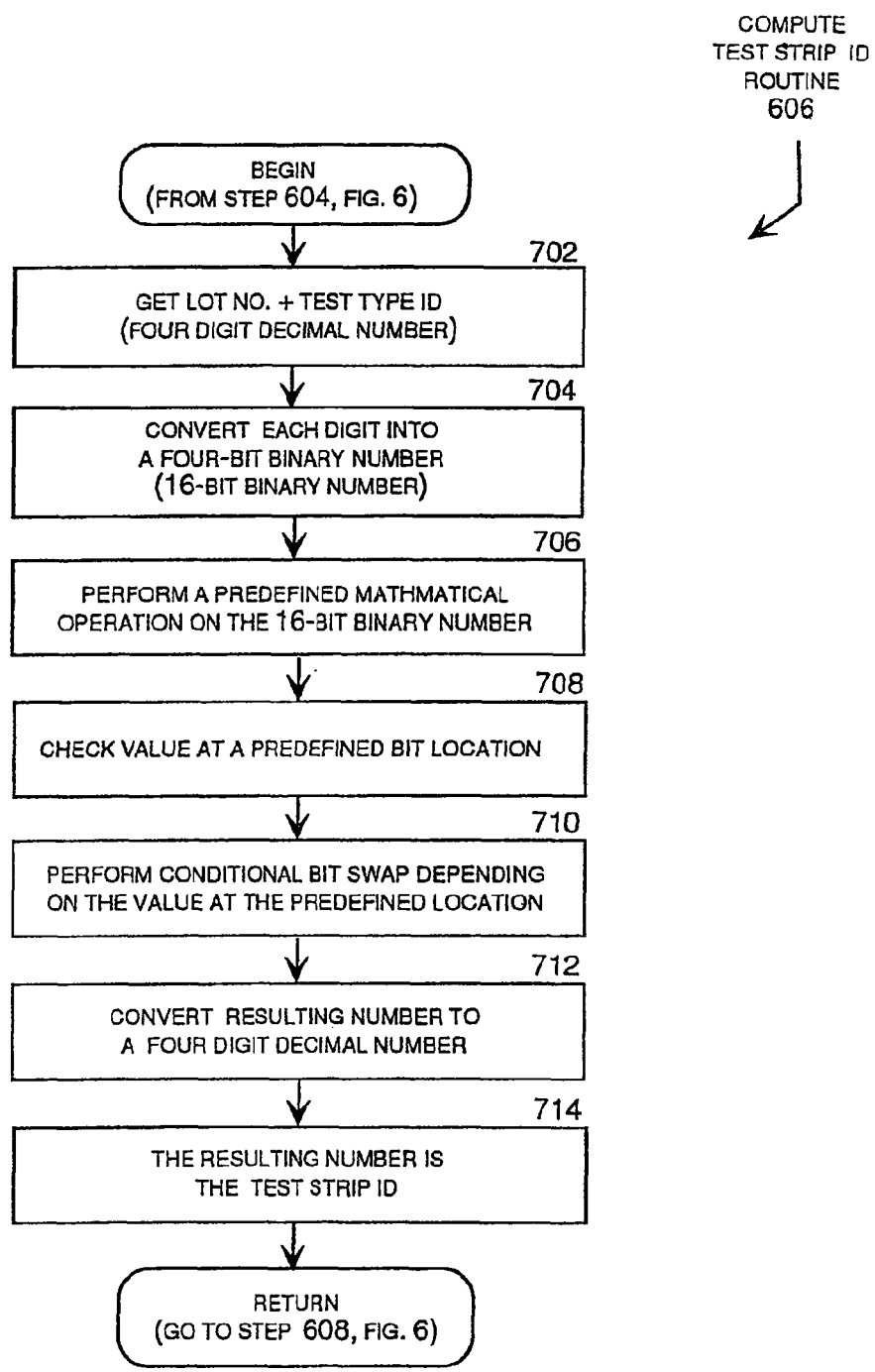
FIG. 7 is a logic flow diagram illustrating a routine for computing a test strip identification number for a health monitoring and diagnostic device.

FIG. 7 is a logic flow diagram illustrating routine 606 for computing a test strip ID for the meter 10. Routine 606 begins following step 604 shown on FIG. 6. In step 702, the meter 10 reads the code number (i.e., lot number plus test type ID) from the romkey. Step 702 is followed by step 704, in which the meter 10 converts this four digit decimal value to 16-bit binary value. Step 704 is followed by step 706, in which the meter 10 applies a predetermined mathematical operation to this 16-bit binary value.

Step 706 is followed by step 708, in which the meter 10 checks a value at a predetermined bit of the 16-bit binary value. Step 708 is followed by step 710, in which the meter 10 performs a conditional bit swap. That is, a first type of bit swap is performed if the value of the checked bit is a "1" and a second type of bit swap is performed if the value of the checked bit is a "0." Step 710 is followed by step 712, in which the meter 10 converts the resulting number to a four digit decimal value. Step 712 is followed by step 714, in which the meter 10 uses the resulting four digit decimal number as the test strip ID. Step 714 is followed by the "RETURN" step, which goes to step 608 on FIG. 6.

The mathematical operation applied in step 706 may be any of a variety of algorithms designed to quasi-randomize the result. For example, the digits may be grouped into subsets that, in turn, are used in one or more linear mathematical operations, such as addition, subtraction, multiplication, division, raising to a power, raising to a fraction, and the like. For example, a polynomial formula may be applied to the digits or subsets of the digits. The digit shuffling operation applied in steps 708 and 710 is also applied to quasi-randomize the result. Many other types of quasi-randomizing methodologies will be apparent to those skilled in the art.

Diagnostic Data Entry

Figure 8:
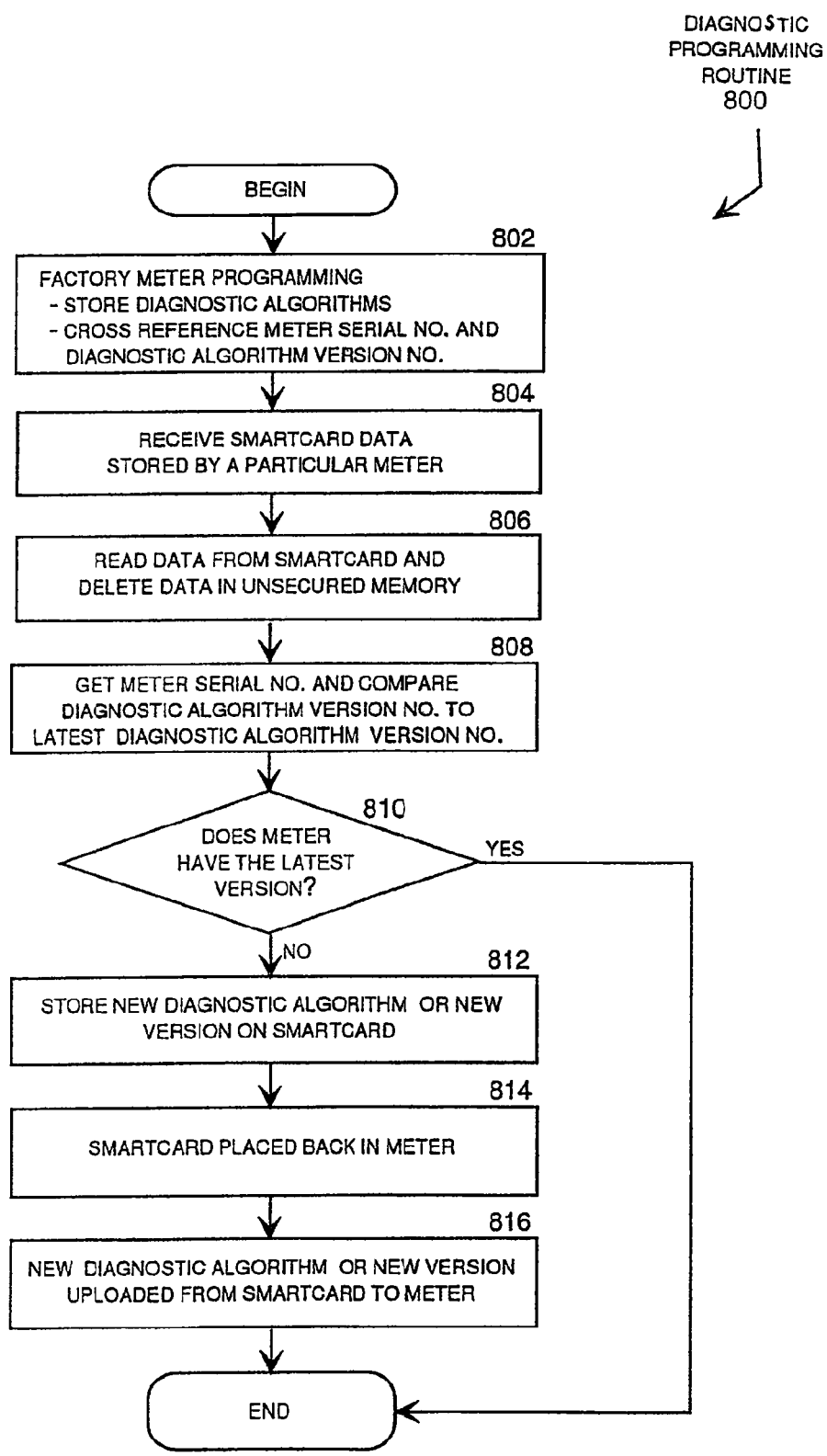
FIG. 8 is a logic flow diagram illustrating a routine for entering diagnostic program modules into a health monitoring and diagnostic device.

FIG. 8 is a logic flow diagram illustrating a routine 800 for entering diagnostic program modules into the meter 10. In step 802, the meter 10 is programmed at the factory with one or more initial diagnostic algorithms. In addition, a computer maintained at the programming site, typically the manufacturer, is programmed with a cross reference table indicating the serial number for the meter and the version number of each diagnostic program module installed in the meter 10.

At some later point, a user downloads medical data from the meter 10 to a smartcard in the course of normal meter use. At this time, the serial number for the meter is also stored on the smartcard. The smartcard is then read by a computer station, which establishes a network connection with a programming server, which may be the same as, or coordinated with, the health report server 102 shown on FIG. 2. At step 804, the programming server receives the data that was stored on the smartcard. Step 804 is followed by step 806, in which the programming server instructs the computer station to erase the unsecured data stored on the smartcard. That is, the computer station erases the medical data stored in the unsecure memory but does not erase the PIN or any data stored in the secure memory.

Step 806 is followed by step 808, in which the programming server gets the serial number for the meter 10 from the received data and looks up the version numbers for the diagnostic program modules installed on the meter. Step 808 is followed by step 810, in which the programming server determines whether the meter 10 includes the latest version of all of the program modules that should be installed on the meter. If the meter 10 includes the latest version of all of the program modules that should be installed on the meter, the "YES" branch is followed to the "END" step, and the meter software is not updated.

If, on the other hand, the meter 10 does not include the latest version of all of the program modules that should be installed on the meter, the "NO" branch is followed to step 812, in which the programming server loads new diagnostic program modules, new versions of diagnostic program modules, or updates for existing program modules on the smartcard. At some later point in step 814, the smartcard is placed back in the meter 10. At this point, step 814 is followed by step 816, in which the new diagnostic program modules, new versions of diagnostic program modules, or updates for existing program modules stored on the smartcard are uploaded to the meter 10. Step 816 is followed by the "END" step.

Diagnostic Analysis

Figure 9:
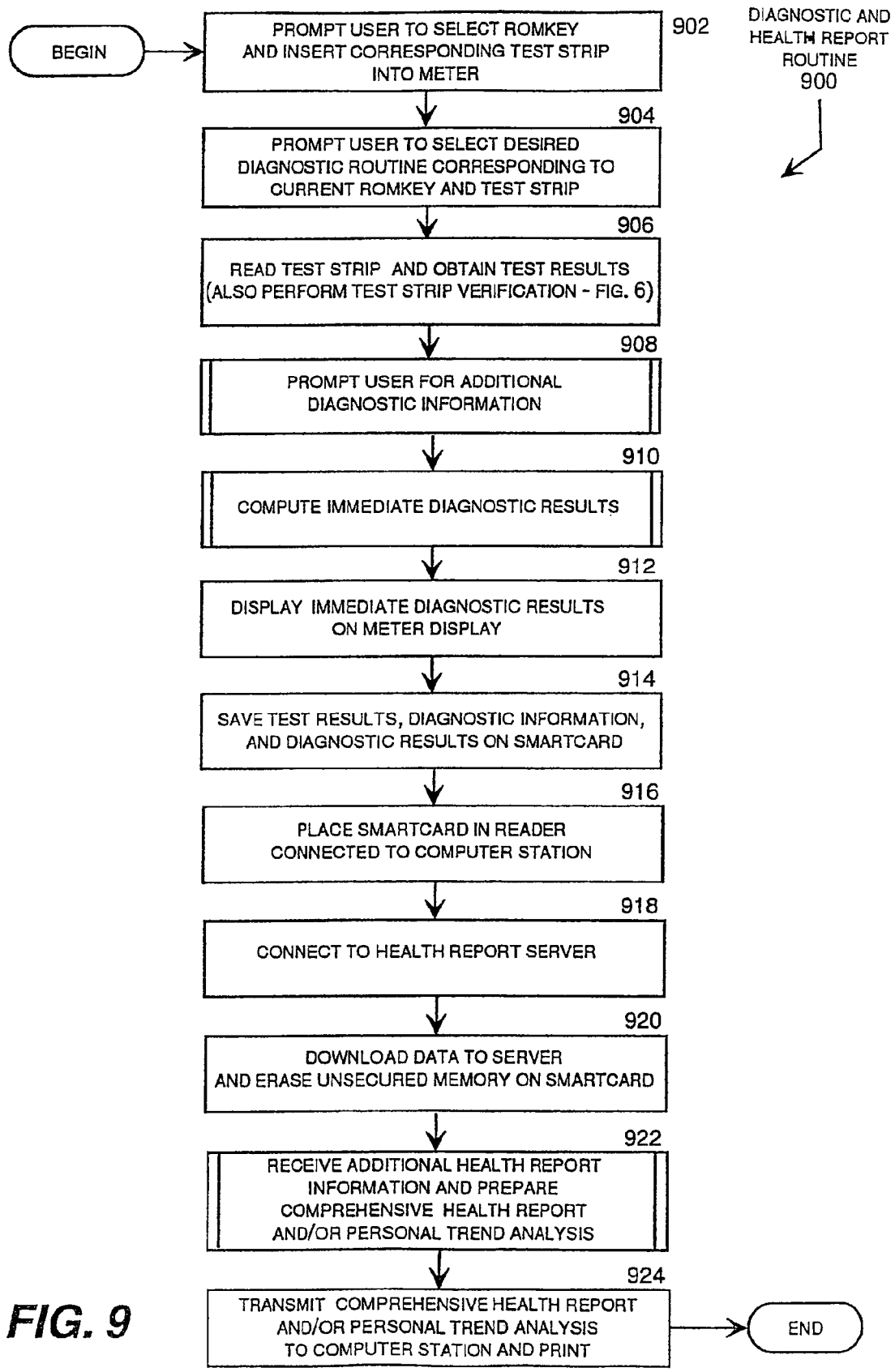
FIG. 9 is a logic flow diagram illustrating a routine for computing immediate diagnostic results in a health monitoring and diagnostic device, and for remotely producing health reports.

FIG. 9 is a logic flow diagram illustrating a routine 900 for computing immediate diagnostic results in the meter 10, and for remotely producing health reports. In step 902, the meter 10 prompts the user to select a romkey and insert a corresponding test strip, with a blood sample, into the meter. Step 902 is followed by step 904, in which the meter 10 prompts the user to select a desired diagnostic program module corresponding to the type of test strip inserted into the meter. Step 904 is followed by step 906, in which the meter 10 performs the test strip verification algorithm shown on FIG. 6 and, if the test strip is verified, obtains test results.

Step 906 is followed by routine 908, in which the meter 10 prompts the user for additional diagnostic information. Routine 908 is described below with reference to FIG. 10. Routine 908 is followed by routine 910, in which the meter 10 computes immediate diagnostic results. Routine 910 is described below with reference to FIG. 11. Routine 910 is followed by step 912, in which the meter 10 displays the diagnostic results on the display device 34. Step 912 is followed by step 914, in which the meter 10 stores the test results, the diagnostic information, and the diagnostic results (and also stores the meter's serial number) on the smartcard.

At some later point, in step 916 the user reads the smartcard with a computer station. Step 916 is followed by step 918, in which the computer station establishes a network connection with the health report server 102. Step 918 is followed by step 920, in which the computer station downloads the data from the smartcard to the health report server 102. Step 920 is followed by routine 922, in which health report server 102 receives additional diagnostic and health report information from the user of the computer station and compiles a personal health report based on the data received from the computer station. Routine 922 is described below with reference to FIG. 12. Routine 922 is followed by step 924, in which the health report server 102 transmits the health report to the computer station, where the health report is printed and delivered to the patient. Step 924 is followed by the "END" step.

Figure 10:
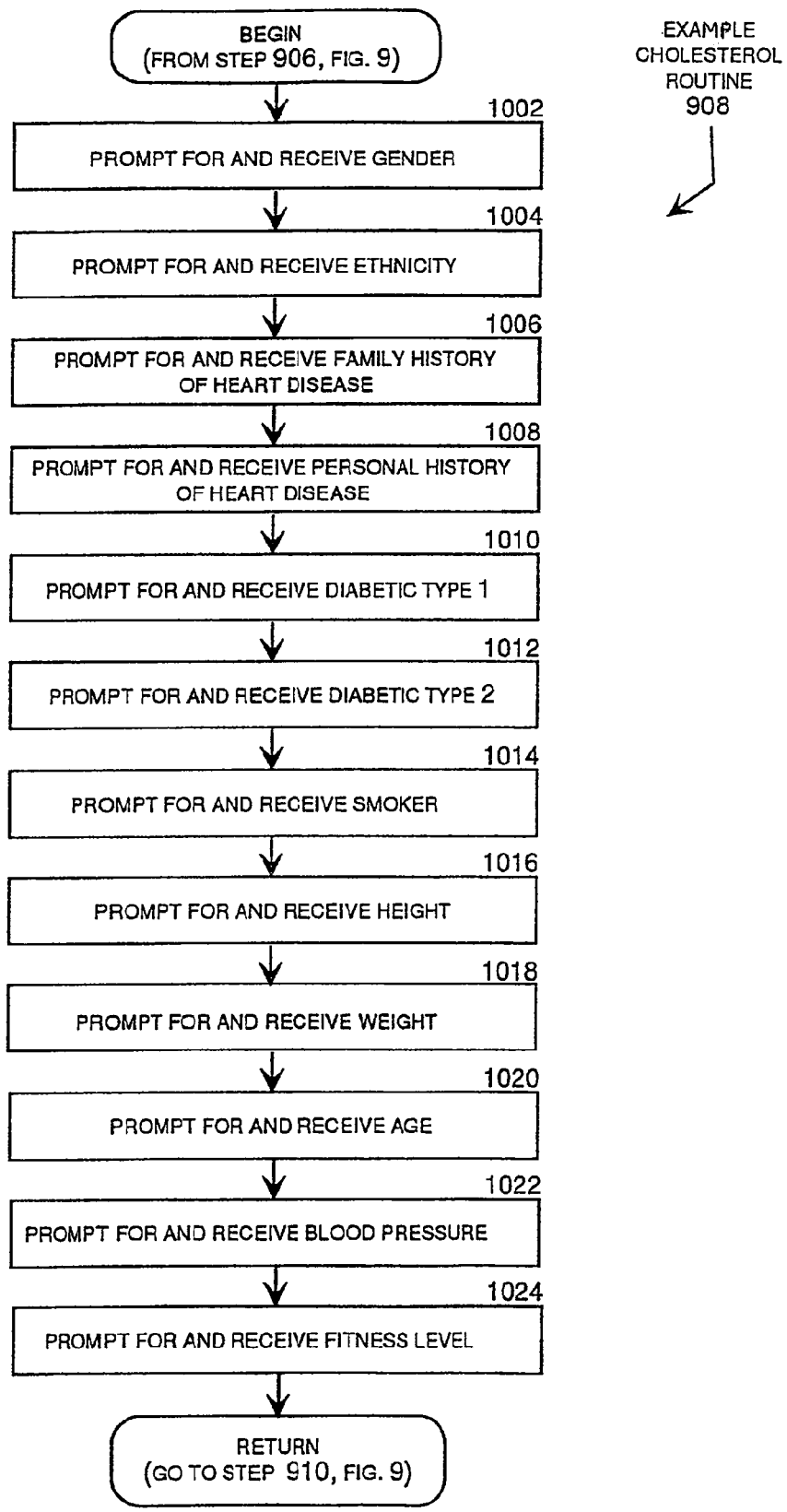
FIG. 10 is a logic flow diagram illustrating a routine for obtaining cholesterol-related diagnostic information for a health monitoring and diagnostic device.

FIG. 10 is a logic flow diagram illustrating routine 908 for obtaining cholesterol-related diagnostic information for the meter 10. Routine 908 begins following step 906 shown on FIG. 9. In step 1002, the meter 10 prompts for and receives the patient's gender. Step 1002 is followed by step 1004, in which the meter 10 prompts for and receives the patient's ethnicity.

Step 1004 is followed by step 1006, in which the meter 10 prompts for and receives an indication of the patient's family history of heart disease. Step 1006 is followed by step 1008, in which the meter 10 prompts for and receives an indication of the patient's personal history of heart disease.

Step 1008 is followed by step 1010, in which the meter 10 prompts for and receives an indication of whether the patient is a type-1 diabetic. Step 1010 is followed by step 1012, in which the meter 10 prompts for and receives an indication of whether the patient is a type-2 diabetic. Step 1012 is followed by step 1014, in which the meter 10 prompts for and receives an indication of whether the patient is a smoker.

Step 1014 is followed by step 1016, in which the meter 10 prompts for and receives an indication of the patient's height. Step 1016 is followed by step 1018, in which the meter 10 prompts for and receives an indication of the patient's weight. Step 1018 is followed by step 1020, in which the meter 110 prompts for and receives an indication of the patient's age. Step 1020 is followed by step 1022, in which the meter 10 prompts for and receives an indication of the patient's blood pressure. Step 1022 is followed by step 1024, in which the meter 10 prompts for and receives an indication of the patient's fitness. Step 1024 is followed by the "RETURN" step, which goes to routine 910 shown on FIG. 9. It will be appreciated that the preceding list of diagnostic information is only illustrative of the type of information that may be gathered, and that less data, different data, or more data could be gathered, if desired.

Figure 11:
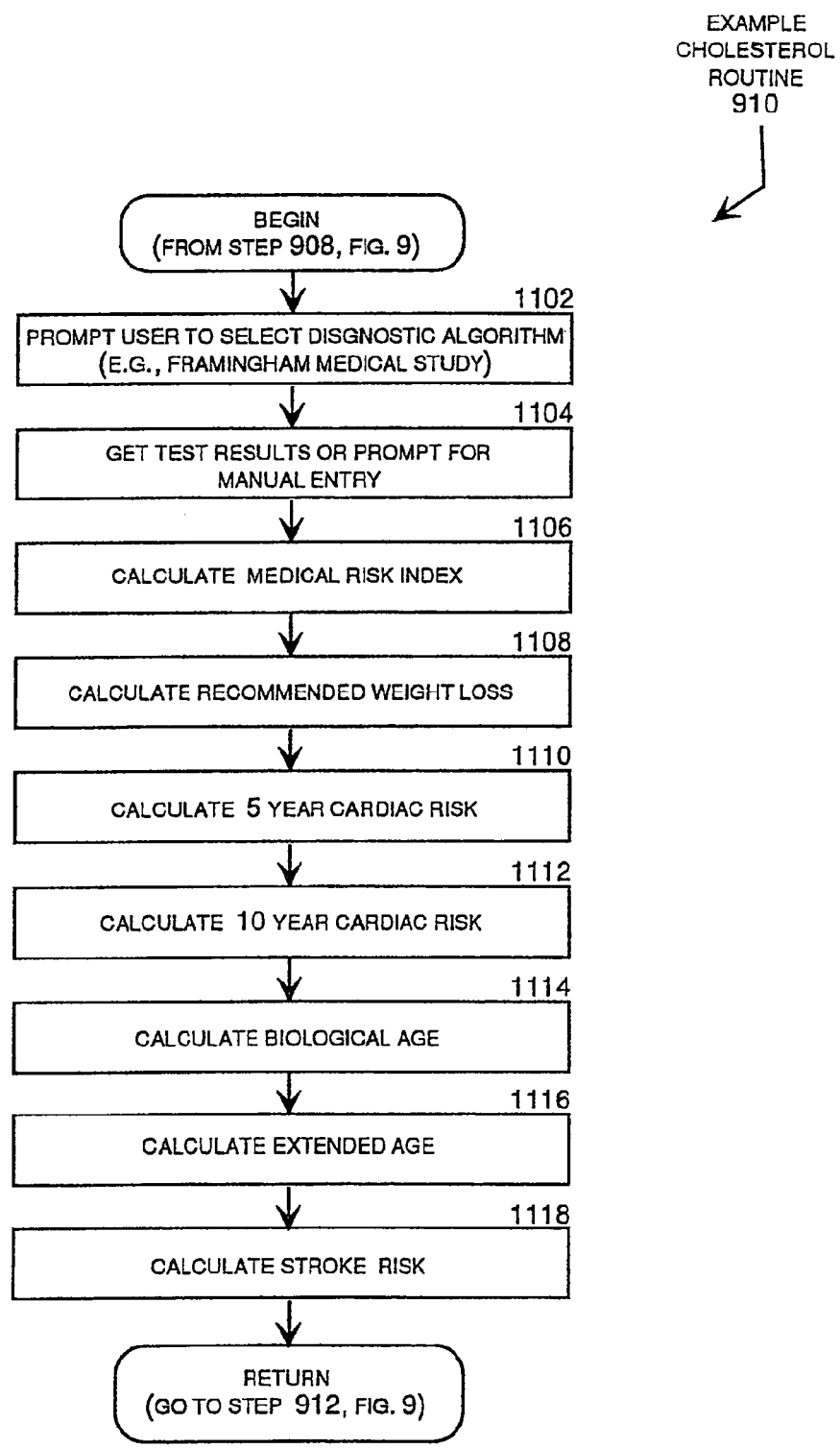
FIG. 11 is a logic flow diagram illustrating a routine for computing immediate cholesterol-related diagnostic results for a health monitoring and diagnostic device.

FIG. 11 is a logic flow diagram illustrating routine 910 for computing immediate cholesterol-related diagnostic results for the meter 10. Routine 910 begins following routine 908 shown on FIG. 9. In step 1102, the meter 10 prompts for and receives a selection of a diagnostic algorithm resident on the meter. Step 1102 is followed by step 1104, in which the meter 10 gets total cholesterol test results from the test instrument module 158 or, if they are not available, prompts the user to input the test results manually.

Step 1104 is followed by step 1106, in which the meter 10 calculates and displays a medical risk index associated with heart disease or heart attack, such as "very high," "high," "moderate," "low," or "very low." Step 1106 is followed by step 1108, in which the meter 10 calculates and displays a recommended weight loss, if appropriate. Step 1108 is followed by step 1110, in which the meter 10 calculates and displays a 5-year cardiac risk (e.g., risk of cardiac arrest in five years is 10%). Step 1110 is followed by step 1112, in which the meter 10 calculates and displays a 10-year cardiac risk (e.g., risk of cardiac arrest in ten years is 20%).

Step 1112 is followed by step 1114, in which the meter 10 calculates and displays a cardiac age (to compare against the patient's chronological age). Step 1112 is followed by step 1114, in which the meter 10 calculates and displays an extended cardiac age (e.g., cardiac age compared to chronological age for five, ten, fifteen, etc. years into the future). Step 1116 is followed by step 1118, in which the meter 10 calculates and displays a medical risk index associated with stroke, such as "very high," "high," "moderate," "low," or "very low." Step 1118 is followed by the "RETURN" step, which goes to step 912 on FIG. 9. It will be appreciated that the preceding list of diagnostic results is only illustrative of the type of information that may be generated, and that less data, different data, or more data could be generated, if desired.

Remote Health Report Generation

Figure 12:
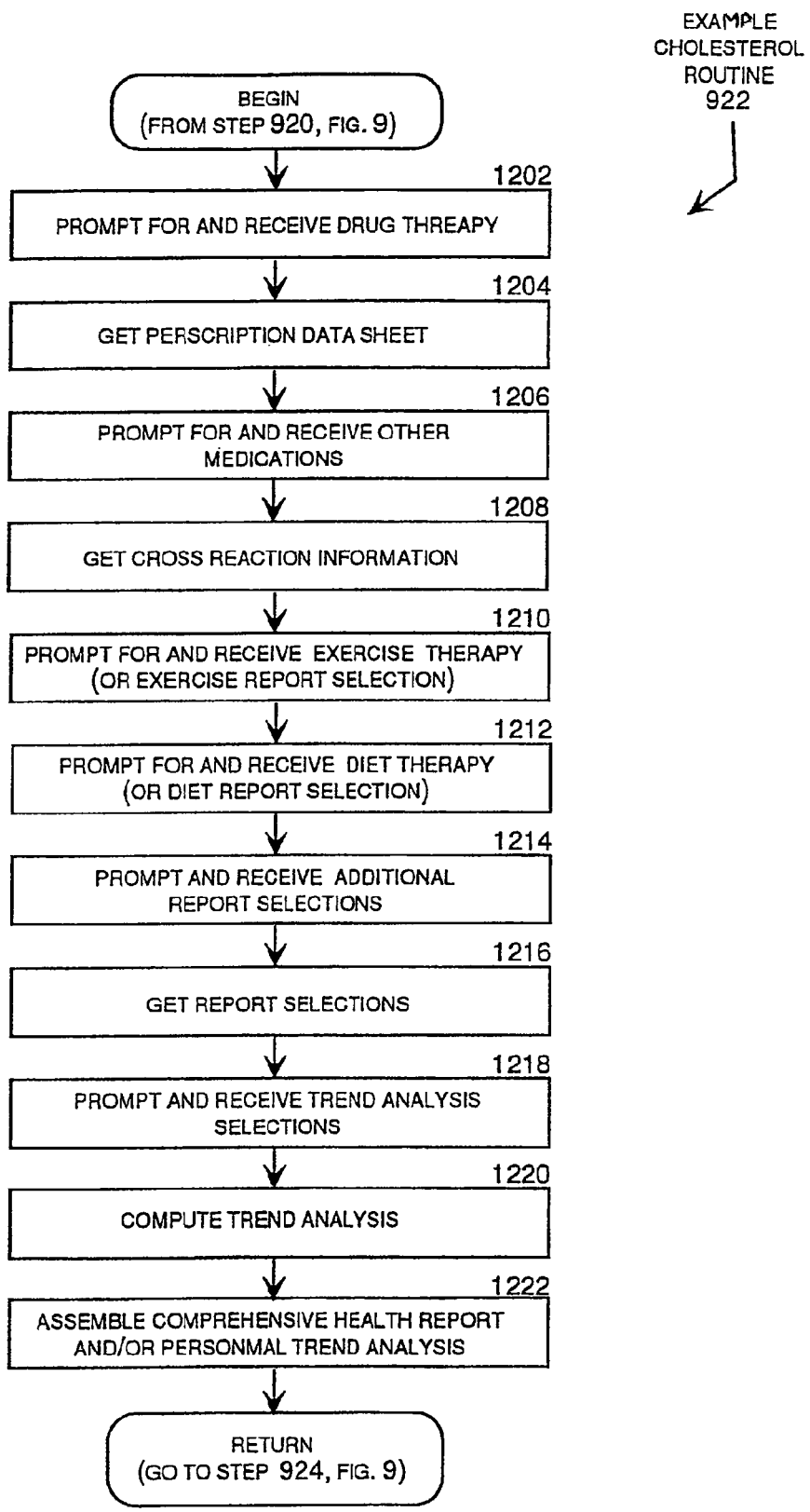
FIG. 12 is a logic flow diagram illustrating a routine for remotely producing health reports.

FIG. 12 is a logic flow diagram illustrating routine 922 for remotely producing health reports. Routine 922 begins following step 920 shown on FIG. 9. In step 1202, in which the health report server 102 prompts for and receives a new drug therapy, such as a cholesterol-lowering prescription. Step 1202 is followed by step 1204, in which the health report server 102 gets a prescription data sheet for the drug therapy. This data sheet typically includes instructions for taking the prescription, such as dosage, times to take each dose, whether to take with food or liquid, whether to avoid driving, pregnancy-related instructions, foods to avoid, and so forth.

Step 1204 is followed by step 1206, in which the health report server 102 prompts for and receives information regarding any other prescription drugs that the patient is currently taking. Step 1206 is followed by step 1208, in which the health report server 102 gets cross-reaction information regarding the new drug therapy and the other current drug prescriptions. Step 1208 is followed by step 1210, in which the health report server 102 prompts for and receives a specific description of exercise therapy for the patient, or a selection of standard exercise sections for inclusion in the health report. Step 1210 is followed by step 1212, in which the health report server 102 prompts for and receives diet therapy for the patient, or a selection of a standard diet section for inclusion in the health report. Step 1212 is followed by step 1214, in which the health report server 102 prompts for and receives indications of additional standard sections for inclusion in the health report.

Step 1214 is followed by step 1216, in which the health report server 102 assembles the preceding information for inclusion in a health report. Step 1216 is followed by step 1218, in which the health report server 102 prompts for and receives trend analysis selections. Step 1218 is followed by step 1220, in which the health report server 102 prepares the selected trend analysis, such as total cholesterol and blood glucose levels over a series of tests. The trend analysis may be provided alone or as part of the health report. Step 1220 is followed by step 1222, in which the health report server 102 assembles the preceding information into a health report and/or trend analysis report. Step 1222 is followed by the "RETURN" step, which goes to step 924 shown on FIG. 9. It will be appreciated that the preceding list of health report information is only illustrative of the type of information that may be compiled, and that less data, different data, or more data could be compiled, if desired.

Smartcard PIN Security

Figure 13:
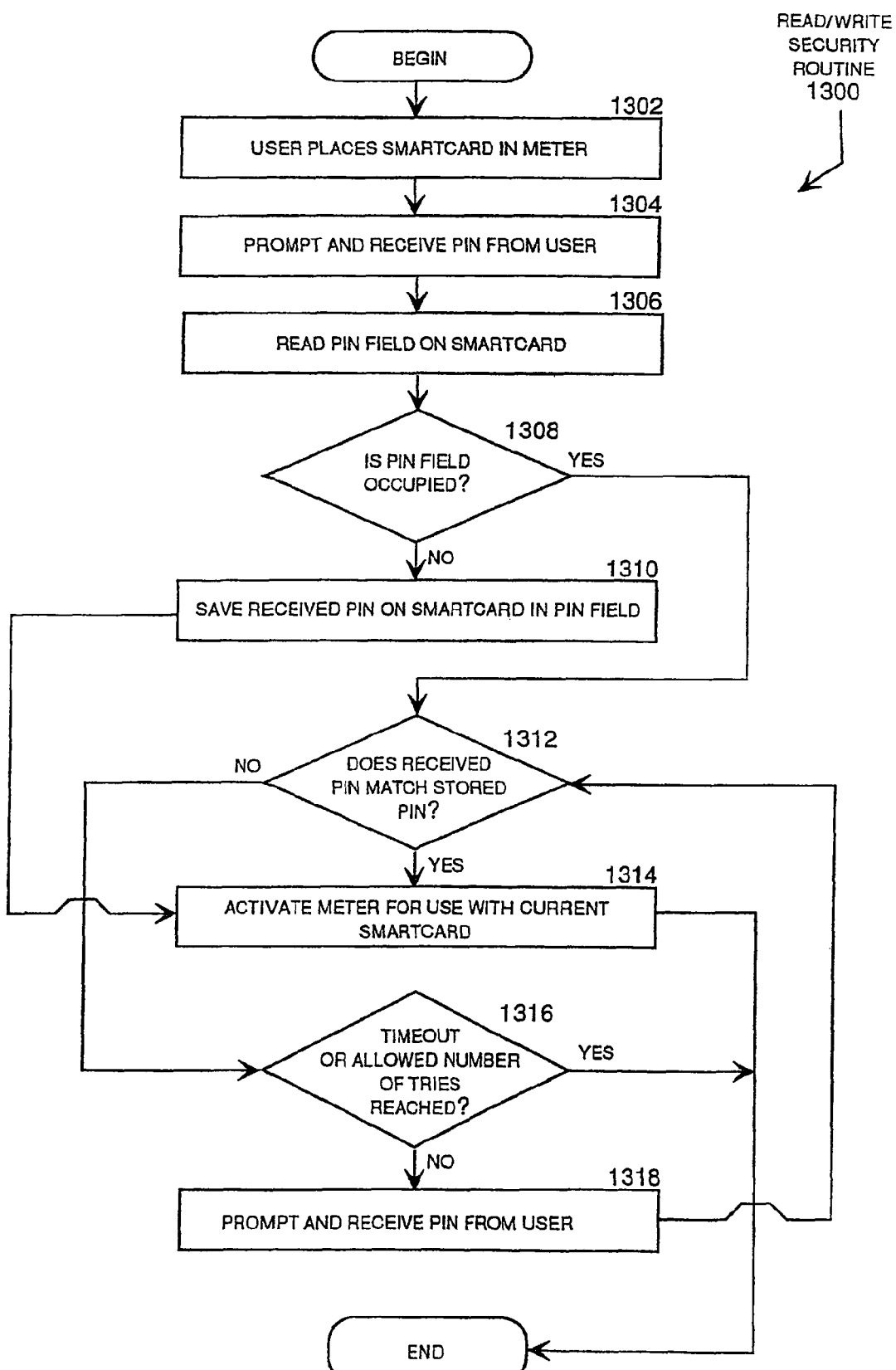
FIG. 13 is a logic flow diagram illustrating a routine for saving medical data to a PIN-secured removable memory storage device for a health monitoring and diagnostic device.

FIG. 13 is a logic flow diagram illustrating a routine 1300 for saving medical data to the PIN-secured removable memory storage device 54, represented by a smartcard. In step 1302, a user places the smartcard in the meter 10. Step 1302 is followed by step 1304, in which the meter 10 prompts for and receives a PIN from the user. Step 1304 is followed by step 1306, in which the meter 10 reads the PIN field on the smartcard. Step 1306 is followed by step 1308, in which the meter 10 determines whether the PIN field is occupied (i.e., whether a PIN has been previously stored on the smartcard).

If the PIN field is not occupied, the "NO" branch is followed from step 1308 to step 1310, in which the meter 10 stores the PIN received from the user in the PIN field on the smartcard. Step 1310 is followed by step 1314, in which the meter 10 activates for use with the current smartcard. Step 1314 is followed by the "END" step.

Referring again to step 1308, if the PIN field is occupied, the "YES" branch is followed to step 1312, in which the meter 10 determines whether the PIN received from the user matches the PIN stored in the PIN field on the smartcard. If the PIN received from the user matches the PIN stored in the PIN field on the smartcard, the "YES" branch is followed to step 1314, in which the meter 10 activates for use with the current smartcard. Step 1314 is followed by the "END" step.

Referring again to step 1312, if the PIN received from the user does not match the PIN stored in the PIN field on the smartcard, the "NO" branch is followed to step 1314, in which the meter 10 determines whether a timeout condition or an allowed number of tries has been reached. If a timeout condition or an allowed number of tries has not been reached, the "NO" branch is followed to step 1318, in which the meter 10 displays an error and prompts the user to reenter the activation code. From step 1318, routine 1300 loops to step 1312. If a timeout condition or an allowed number of tries has been reached, the "YES" branch is followed from step 1316 to the "END" step, and the meter 10 is not activated for use with the instant smartcard.

Secure Medical Records Maintenance System

Figure 14:
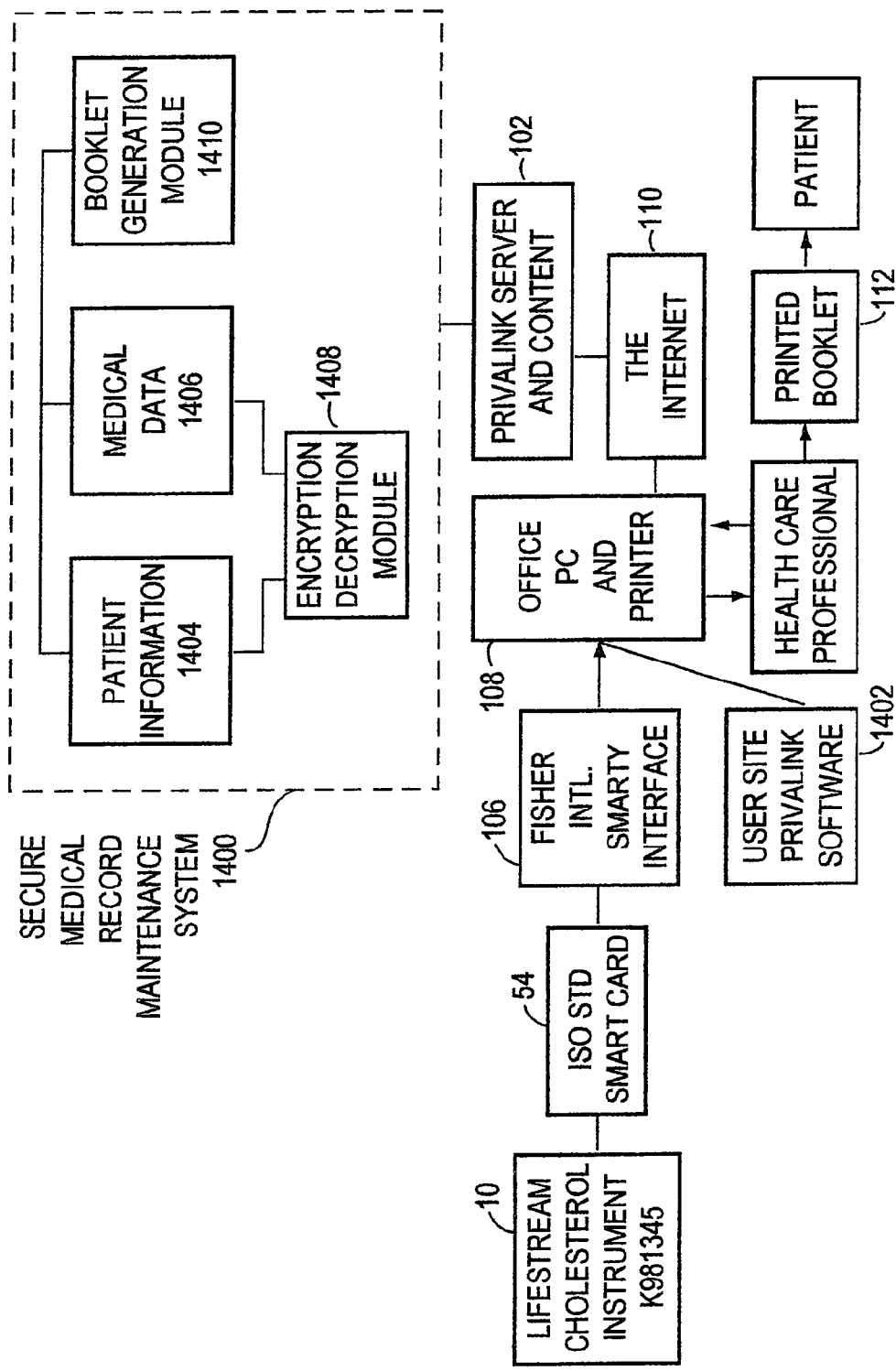
FIG. 14 is a functional block diagram of a system for using a health monitoring and diagnostic device in connection with a secure medical records maintenance system.

FIG. 14 is a functional block diagram of a system for using the meter 10 in connection with a secure medical records maintenance system 1400. The meter 10 stores a patient's test results and diagnostic information on a removable memory storage device, such as the smartcard 54. A conventional interface 106 may then be used to interface the smartcard 54 with a conventional desktop, laptop or other type of computer 108, which in turn communicates with other computers over a network-based computer system, such as the Internet 110. As discussed previously, this Internet link may be used to produce a printed health report booklet 112 including a health assessment based on a patient's test results and diagnostic information, which a health-care provider typically provides to the patient.

Although this secure medical records maintenance system 1400 is specifically adapted for use with the meter 10, it may be used to store any type of electronic medical records, and is particularly convenient for storing a wide range of electronic medical data generated remotely from the hospital or doctor's office environment. In addition, the secure medical records maintenance system 1400 may read medical data stored on memory storage devices other than the smartcard 54, and may operate over computer networks other than the Internet 100.

The secure medical records maintenance system 1400, which is presently known as the "PRIVALINK" system, operates in connection with a software module 1402 installed on the accessing computer 108. This software is presently known as the "PRIVALINK" user site software. The server-side "PRIVALINK" system 1400 includes a first remote server 1404 that stores patient identification information, a second remote server 1406 that stores patient medical data, an encryption/decryption module 1408 that implements encryption and other security-related functions, and a booklet generation module 1410, which produces printed health report booklets 112 based on the information stored in the servers 1404, 1406. The patient identification information and medical data are maintained in separate, secure servers 1404, 1406 to prevent correlation of a specific patient's medical data with the associated patient identification information.

Because the data on the servers 1404, 1406 is separate and secure from each other, access may be granted to either server without identifying any particular patient's medical data. For example, access may be granted to the first remote server 1404, but not to the second server 1406, for the purpose of generating a mailing list of patients without divulging any medical data associated with the patients. Similarly, access may be granted to the second remote server 1406, but not to the first server 1404, for the purpose of conducting investigative analyses involving patient medical data without divulging any patient identification information associated with the medical data.

For further data security and because each smartcard 54 only has a limited data storage capability, the medical data stored on each smartcard may be automatically erased from the smartcard after the data is entered into the second remote server 1406. To obtain the medical data, the smartcard 54 is received within the meter 10, which stores the medical data on the smartcard. And to download the medical data to the medical records maintenance system 1400, the removable memory storage device is receivable within the interface 106 for communication with the computer 108, which is operable for transmitting the medical data to the second remote server 1406 over the Internet 110.

Figure 15:
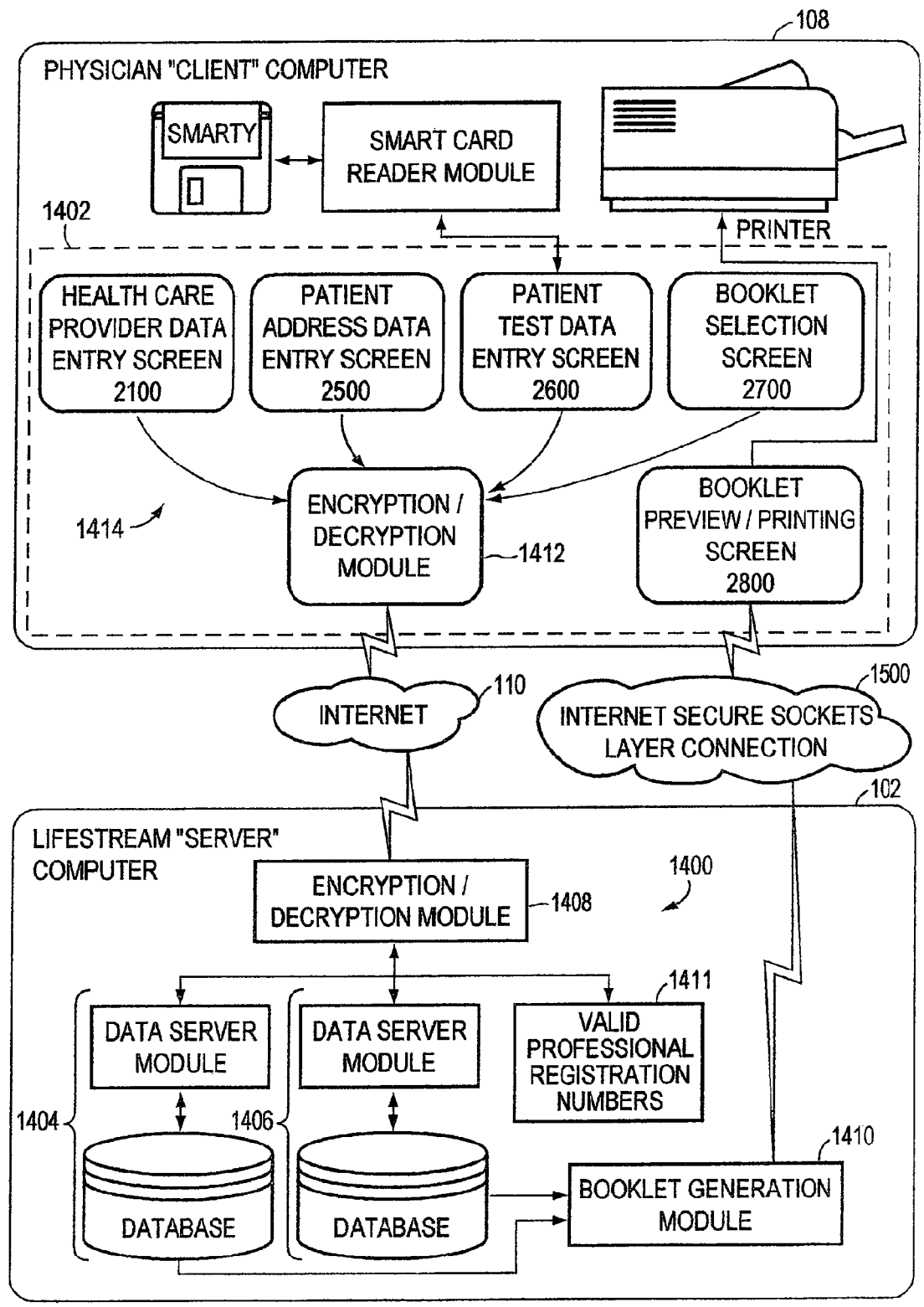
FIG. 15 is software architecture diagram illustrating a system for conducting secure communications between a health monitoring and diagnostic device and a secure medical records maintenance system.

FIG. 15 is software architecture diagram illustrating a system for conducting secure communications between the computer 108 and the secure medical records maintenance system 1400. The "PRIVALINK" user site software 1402 includes an encryption/decryption module 1412 that implements encryption/decryption services on the client computer 108. A corresponding encryption/decryption module 1408 on the secure medical records maintenance system 1400 implements complimentary encryption/decryption services on the server side, typically using a well-known encryption/decryption package, such as that known as "BLOWFISH" or "DES." The server-side encryption/decryption module 1408 also maintains access to a table of valid professional registration numbers 1411, typically DEA numbers, received from the registering agency. This table is used to validate the professional registration numbers of practitioners attempting to access the secure medical records maintenance system 1400.

The server-side encryption/decryption module 1408 also maintains a record of all transactions with accessing computers for future analysis. In addition, all data transfers from the secure medical records maintenance system 1400 to the user site 108, such as health report booklets 112, are encrypted/decrypted through an Internet secure sockets layer connection 1500, which is well known to those skilled in the art. These encryption/decryption services prevent theft or inadvertent loss of patient medical data through unintended transmission or extraction of communications occurring on the Internet 110.

The "PRIVALINK" user site software 1402 also implements client application, certification and login processes for accessing the secure medical records maintenance system 1400. The application, certification and login process is described below with reference to FIGS. 17-19. Upon successful login to the secure medical records maintenance system 1400, the "PRIVALINK" user site software 1402 implements a menu-driven user interface system 1414 for conducting communications between the practitioner computer 108 and the secure medical records maintenance system 1400. This interface system includes a health care provider data entry screen 2100 shown in FIG. 21, a patient address data entry screen 2500 shown in FIG. 25, a patient test data entry screen 2600 shown in FIG. 26, a booklet selection screen 2700 shown in FIG. 27, and a booklet preview/printing screen 2800. The menu-driven user interface system 1412 also includes other related user interface screens. The operation of the menu-driven user interface system 1412 is described below with reference to FIG. 17.

Figure 16:
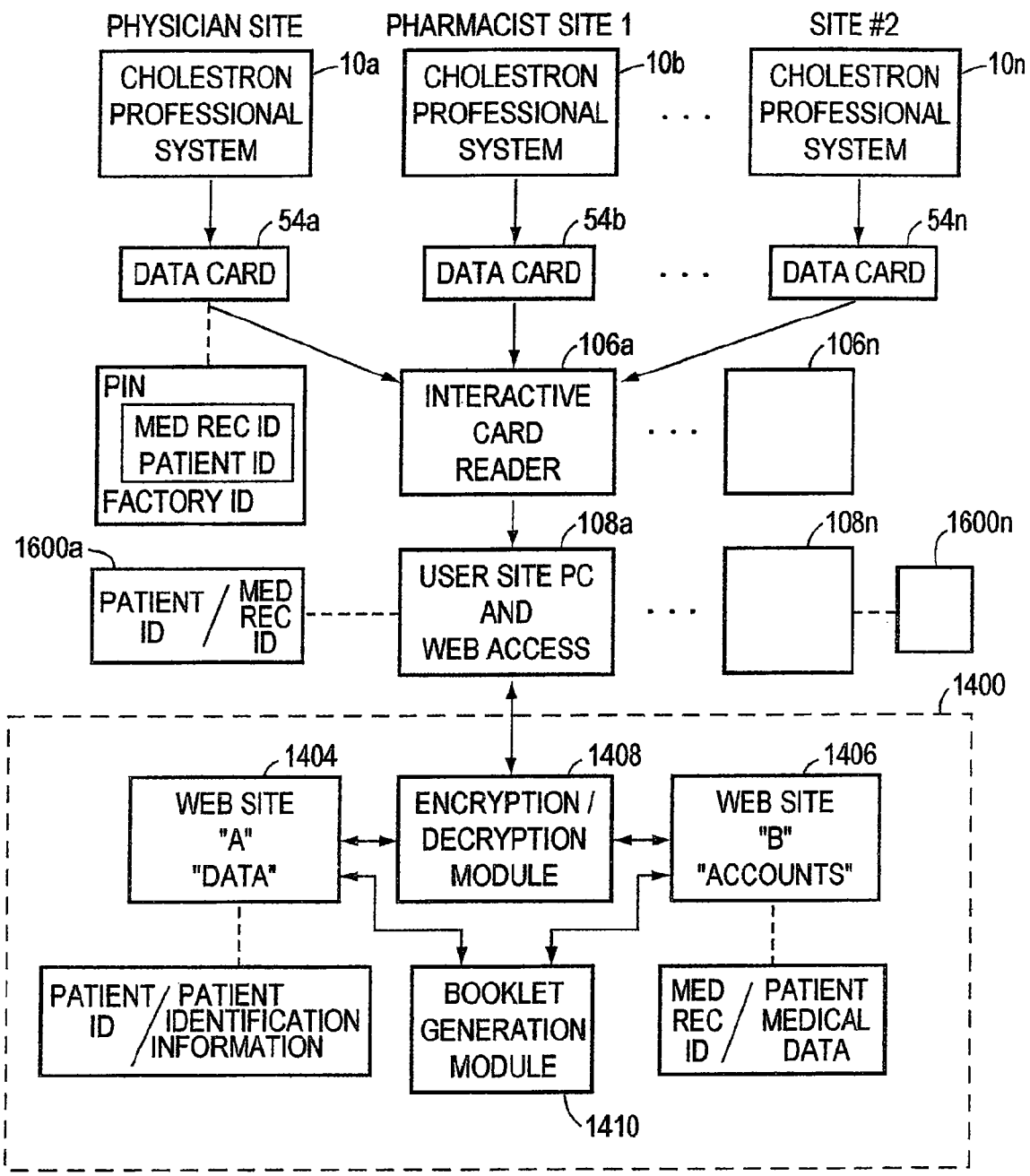
FIG. 16 a functional block diagram illustrating security aspects of a secure medical records maintenance system.

FIG. 16 a functional block diagram illustrating security aspects of the secure medical records maintenance system 1400. The secure medical records maintenance system 1400 preferably includes a large number of smartcards 54*a-n*, which operate in concert with a large number of meters 10*a-n*. Although each smartcard 54*a-n* is preferably used to store medical data for an associated patient, each card could be used to store medical data for multiple patients. Each smartcard 54 also stores a patient-specified personal identification number (PIN), and may store PINs for multiple patients if the smartcard is configured to store medical data for multiple patients. Each PIN is used to gain access to a secure storage area on the smartcard 54, which stores an associated patient identification number and medical records identification number, which are assigned by the secure medical records maintenance system 1400.

The first remote server 1404 of the secure medical records maintenance system 1400 stores patient identification information indexed by patient identification numbers, and the second remote server 1406 stores patient medical data indexed by the medical records identification numbers. Typically, each patient identification number and medical identification number is a unique number assigned by the operator of the secure medical records maintenance system 1400 upon entry of each patient into the system. For example, the patient identification numbers and medical identification numbers may be social security numbers or sequential registration numbers. Alternatively, the patient identification numbers and medical identification numbers may be unique numbers computed by a non-repeating pseudo-random number generator. The patient identification number and the medical records identification number may be 16-bit hexadecimal or another suitable value. In addition, either or both of the patient identification number and the medical records identification number may be a global user identification number (GUID), which is a secure communication key generated by well-known secure encryption systems, such as currently available private-key and public-key encryption systems including "BLOWFISH," "DES" and others. Many other schemes for assigning unique patient identification numbers will become evident to those skilled in the art.

For security purposes, the medical data maintained in the second remote server 1406 cannot be correlated to the associated patient identification information maintained in the first remote server 1408 based on the information contained in the first and second remote servers. To allow correlation of the data stored in the two servers 1404, 1406 the secure medical records maintenance system 1400 includes a correlation table 1600 uniquely associating each medical records identification number with a particular one of the patient identification numbers. The correlation table 1600 for a particular patient typically resides in the PIN-secured storage area on the patient's smartcard 54. The correlation table 1600 for a practitioner's patients may also reside on the practitioner's computer 108, such as a doctor's or pharmacist's computer, that is associated with a licensed medical practitioner having an assigned professional registration number (DEA number). Each practitioner's correlation table 1600 is preferably encrypted and maintained in a secure file. The proprietor of the secure medical records maintenance system 1400 may also maintain a complete back-up correlation table 1600, typically in a secure encrypted file located on a separate file server.

For further security, the first and second remote servers 1404, 1406 are accessed by the practitioners' computers 108*a-n* through encrypted communications secured by an application procedure that includes validation of the practitioner's registration number (DEA number). This access will be limited to medical records and patient identification information associated with the accessing practitioner. In other words, each practitioner will only have access to his or her patients' medical records and patient identification information.

Similar access procedure may be implemented for individual patients, except that access will be limited to that particular patient's medical records and patient identification information. For example, individual patients may register in advance with the proprietor of the system 1400, which will issue each patient a unique registration number. In this case, the first and second remote servers 1404, 1406 may accessed by computers operated by the individual patients through encrypted communications secured by an application procedure that includes validation of the patient's registration number.

For both practitioners and individual patients, the application procedure may be further secured by receipt and validation of a client-supplied PIN. Moreover, the application procedure typically includes issuance of a client certificate insuring that access to the first and second remote servers occurs from the client computer that initiated the application and certification process.

Those skilled in the art will appreciate that the data distribution system implemented by the secure medical records maintenance system 1400 includes many aspects of data security. For example, a patient's medical records identification number cannot be obtained from the patient's smartcard 54 without access to the patient-assigned PIN. In addition, while the patient's medical data is indexed by the patient's medical records identification number in the second server 1406, the patient's name and other identification information cannot be retrieved from the first server 1404 using this data. Similarly, a hacker obtaining assess to one or both of the servers 1404, 1406 cannot correlate patient identification information with patient medical data. In addition, the correlation data for the entire secure medical records maintenance system 1400 is distributed among the various smartcards 54*a-n* and practitioner computers 108*a-n* registered for use with the system. Thus, a hacker cannot obtain the correlation data for any single patient, much less the entire database, through access to the centrally-maintained data servers 1404, 1406.

For further security, the secure medical records maintenance system 1400 cannot be accessed from the a medical practitioner's computer 108 without knowledge of the proper practitioner-assigned PIN. And all communication between the practitioner's computer 108 and the secure medical records maintenance system 1400 are encrypted for transmission security. Furthermore, each correlation table 1600, which provides the link between patient identification numbers and medical records identification numbers for a particular practitioner, may itself be encrypted, with the key to this encryption stored in a separate location. For example, this encryption key may be a practitioner PIN or GUID stored on a PIN-secured area the practitioner's computer 108 or on a smartcard 54 assigned to the practitioner.

Figure 17:
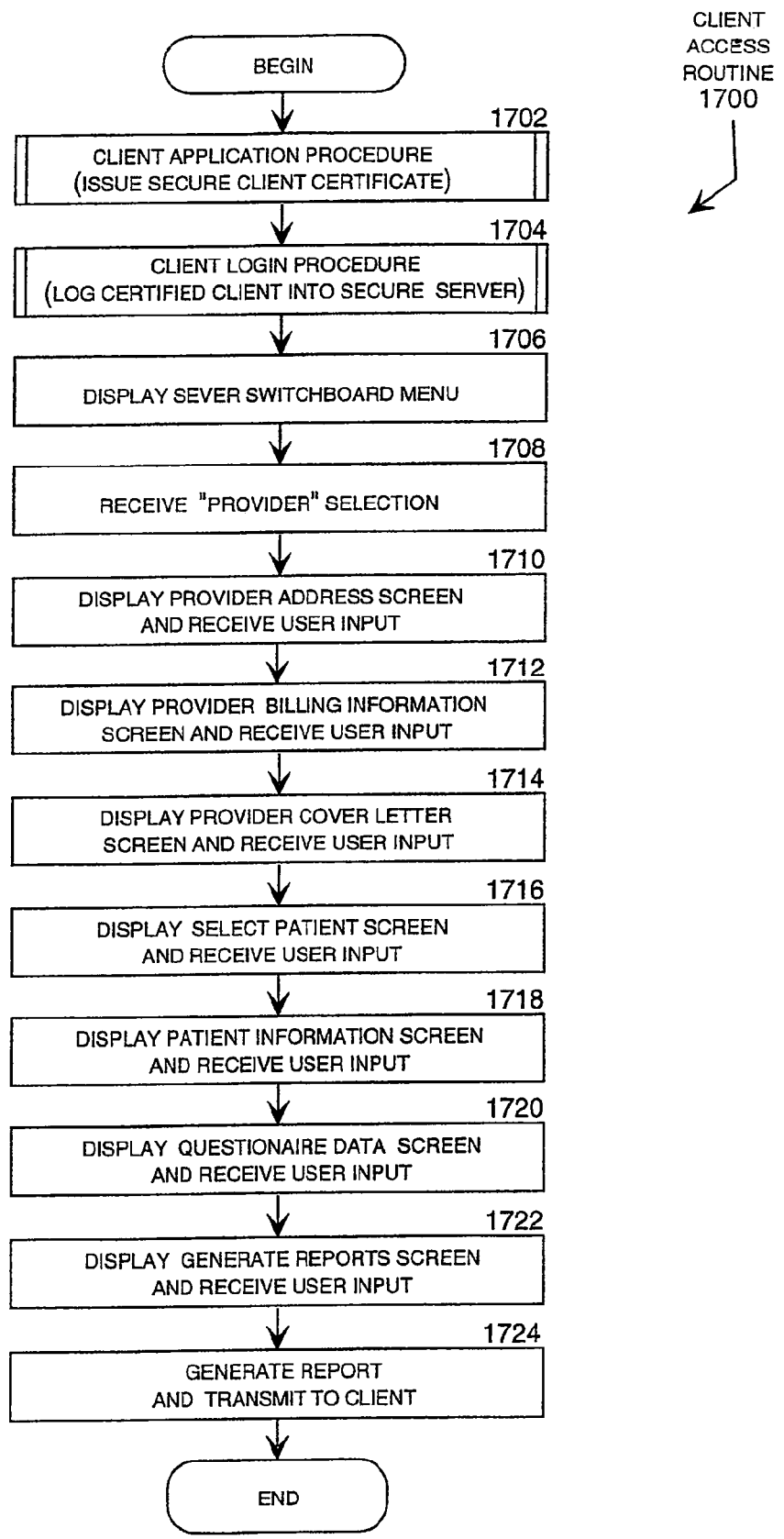
FIG. 17 is a logic flow diagram illustrating a process for a communicating with a secure medical records maintenance system.

FIG. 17 is a logic flow diagram illustrating an illustrative process 1700 for communicating with the secure medical records maintenance system 1400. In routine 1702, a medical practitioner conducts a client application procedure to obtain a secure client certificate, which is also known as a "CA" or certificate-authentication. Routine 1702 is described in greater detail with reference to FIG. 18. Routine 1702 is followed by a client login procedure 1704, which is described in greater detail with reference to FIG. 19. These procedures ensure that access to the secure medical records maintenance system 1400 is limited to registered medical practitioners using the same computer and browser that the practitioner used to obtain a secure client certificate through the application procedure. That is, any attempt to access the secure medical records maintenance system 1400 by a person without a valid DEA number, or from a non-certified computer or browser, will be rejected. As noted previously, similar procedures may be implemented for allowing individual patients to access their records on the secure medical records maintenance system 1400.

Figure 18:
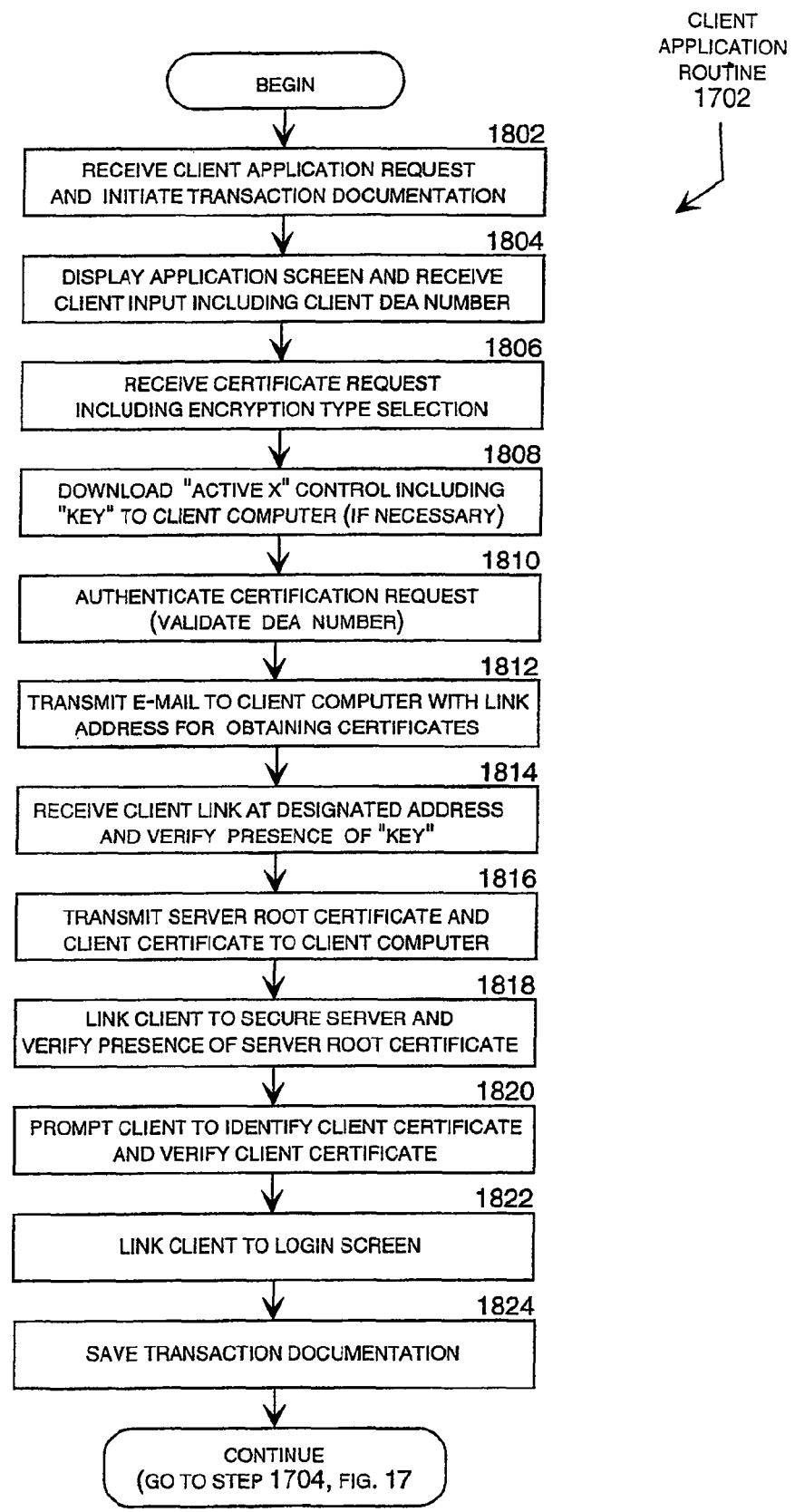
FIG. 18 is a logic flow diagram illustrating a process for applying for access to a secure medical records maintenance system.

FIG. 18 is a logic flow diagram illustrating routine 1702 used by a medical practitioner to apply for access to the secure medical records maintenance system 1400. Routine 1702 begins at the start of FIG. 17. In step 1802, the client-side PRIVALINK software 1402 issues a client application request to the server-side encryption/decryption module 1408, which initiates a transaction document record for the communication. That is, all communications between the client-side PRIVALINK software 1402 and the server-side encryption/decryption module 1408 are recorded for future analysis by the server-side encryption/decryption module 1408. The client application request is typically received by an Internet link to a specified web page associated with the server-side encryption/decryption module 1408. The medical practitioner can obtain the proper Internet address by placing a telephone call to the operator of the system 1400. The phone number, and possibly the Internet address, will be printed on each meter 10 and may also be available through other forms of notification, such as advertisement and direct-mail notification to licensed practitioners (e.g., physicians and pharmacists).

Step 1802 is followed by step 1804, in which the PRIVALINK software 1402 displays an application screen and receives client input including the practitioner's professional registration number, typically a DEA number. Step 1804 is followed by step 1806, in which the PRIVALINK software 1402 receives a certification request including selection of an encryption type. This is typically associated with completion of the data-entry fields of the application screen and selection of a "submit" control item. Step 1806 is followed by step 1808, in which the PRIVALINK software 1402 downloads an encryption program module from the server-side encryption/decryption module 1408, such as an "ACTIVE X" control or applet, to the client's computer 108. This encryption program module typically includes a "key" or nugget of information to be stored in the accessing browser. The server-side encryption/decryption module 1408 can later check an accessing computer for the presence of the "key" to ensure that the accessing computer and browser is the same as the one going through the application procedure.

Step 1808 is followed by step 1810, in which the server-side encryption/decryption module 1408 validates the registration number (e.g., DEA number) entered by the applicant, typically by comparing the received registration number to the table of valid registration numbers 1411 received from the registration authority (e.g., table of valid DEA numbers). If the registration number is properly validated, step 1810 is followed by step 1812, in which the server-side encryption/decryption module 1408 transmits an e-mail message to the PRIVALINK software 1402 including a URL for accessing the secure servers 1404, 1406. Step 1812 is followed by step 1814, in which the PRIVALINK software 1402 transmits a client link to the designated URL. Upon receipt of the link, the server-side encryption/decryption module 1408 checks for the presence of the "key" to ensure that the accessing computer and browser is the same as the one that went-through the application procedure.

If the "key" is properly validated, step 1814 is followed by step 1816, in which the server-side encryption/decryption module 1408 transmits a "server root CA" and a "client certificate" to the PRIVALINK software 1402 on the client's computer 108. Step 1816 is followed by step 1818, in which the PRIVALINK software 1402 links the applicant to a secure area of the encryption/decryption module 1408, which validates the presence of the server root CA. If the server root CA is properly validated, step 1818 is followed by step 1820, in which the PRIVALINK software 1402 prompts the user to identify the client certificate for use in the transaction. If the client certificate is properly validated, step 1820 is followed by step 1822, in which the PRIVALINK software 1402 links the applicant to a login screen. Step 1822 is followed by step 1824, in which the encryption/decryption module 1408 saves the transaction documentation for the client's application procedure. Step 1824 is followed by the "CONTINUE" step, which returns to routine 1704 shown in FIG. 7.

Figure 19:
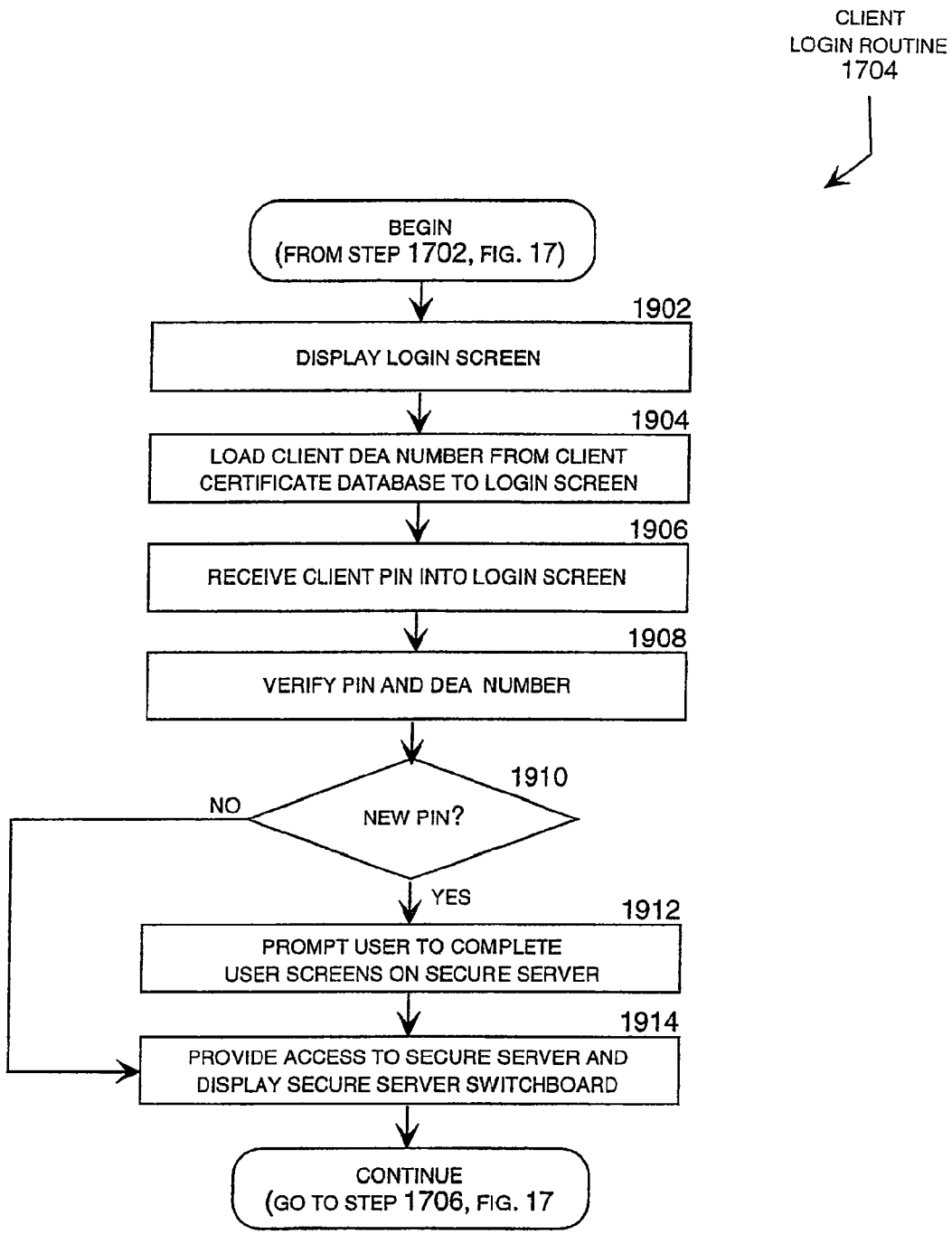
FIG. 19 is a logic flow diagram illustrating a process for logging into a secure medical records maintenance system.

FIG. 19 is a logic flow diagram illustrating a routine 1704 for logging into the secure medical records maintenance system 1400. Routine 1704 begins following routine 1702 shown in FIG. 7. In step 1902, the PRIVALINK software 1402 displays a login screen on the client's computer 108. Step 1902 is followed by step 1904, in which the PRIVALINK software 1402 loads the client's registration number, which was obtained during the application procedure described with reference to FIG. 18, into the login screen. That is, an accessing client does not have an opportunity to enter the login procedure without having first having gone through the application procedure described with reference to FIG. 18, which requires the applicant to provide a valid registration number, which typically may be a DEA number for a licensed medical practitioner or a registration number issued by the proprietor of the secure medical records maintenance system 1400 for an individual patient.

Step 1904 is followed by step 1906, in which the PRIVALINK software 1402 receives the practitioner's personal identification number (PIN). Step 1906 is followed by step 1908, in which the encryption/decryption module 1408 validates the practitioner's personal identification number (PIN) for use with the received professional registration number. Step 1908 is followed by step 1910, in which the encryption/decryption module 1408 determines whether the received PIN is a new PIN for use in connection with the received professional registration number. If the received PIN is a new PIN for use in connection with the received professional registration number, the "YES" branch is followed from step 1910 to step 1912, in which the PRIVALINK software 1402 prompts the user to complete the interface screens 2000-2007 (FIGS. 20-27). Step 1912 and the "NO" branch from step 1910 are followed by step 1914, in which the client is linked to the interface screens 2000-2007 (FIGS. 20-27). Step 1914 is followed by "CONTINUE" step, which returns to step 1706 shown on FIG. 7.

User Interface Design

Figures 20, 21:
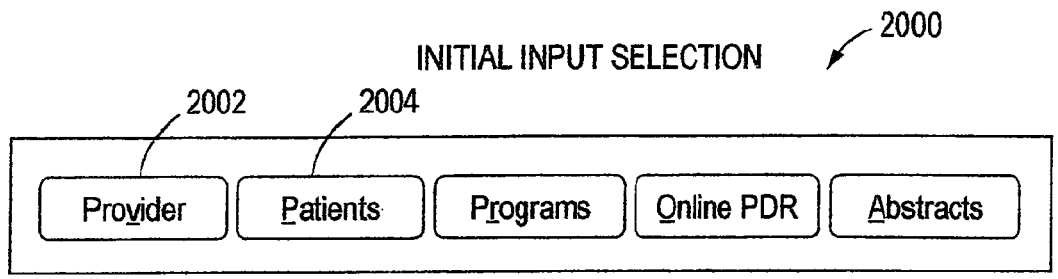
FIG. 20 is an illustration of a "switchboard" user interface in a secure medical records maintenance system.
FIG. 21 is an illustration of an "address" user interface in a secure medical records maintenance system.

Referring again to FIG. 17, once the medical practitioner has successfully logged into the secure medical records maintenance system 1400, routine 1704 is followed by step 1706, in which the PRIVALINK software 1402 displays a "switchboard" user interface 2000. FIG. 20 is an illustration of a typical "switchboard" user interface 2000, which includes a number of selection items corresponding to functions available on the server. For example, the interface 2000 typically includes a "provider" selection item 2002 and a "patients" selection item 2004. To illustrate the operation of the user interface it is assumed that the practitioner initially selects the "provider" selection item 2002. Thus, step 1706 is followed by step 1708, in which the PRIVALINK software 1402 receives a "provider" selection from the "switchboard" user interface 2000.

Step 1708 is followed by step 1710, in which the PRIVALINK software 1402 displays an "address" user interface 2100. FIG. 21 is an illustration of a typical "address" user interface 2100. The interface 2100 includes a first field 2102 for entering a practitioner registration number, typically a DEA number, and a second field 2104 for entering a practitioner-assigned PIN. The interface 2100 also includes a number of other fields for entering the practitioner's contact information, such as address, phone number, and so forth. The interface 2100 also includes an "address" tab 2106, a "billing info" tab 2108, and a "cover letter" tab 2110 displayed adjacent to the user interface 2100. These tabs allow the user to toggle among corresponding user interface screens. As noted above, the interface 2100 initially appears in a "default" mode with the "address" tab 2106 selected.

For example, step 1710 may be followed by step 1712, in which the PRIVALINK software 1402 displays a "billing info" user interface in response to user selection of the "billing info" tab 2108. FIG. 22 is an illustration of a typical "billing information" user interface 2108. The interface 2100 includes a number of fields 2202 for entering payment authorization, such as a bank credit or debit card number. The interface 2100 may include other types of payment options, such as a bank account number for wire transfers, authorization to include the charges on a telephone bill or Internet service provider bill associated with the Internet link to the server-based system 1400, reference to an authorized account for billing at a later date, and the like.

Figure 23:
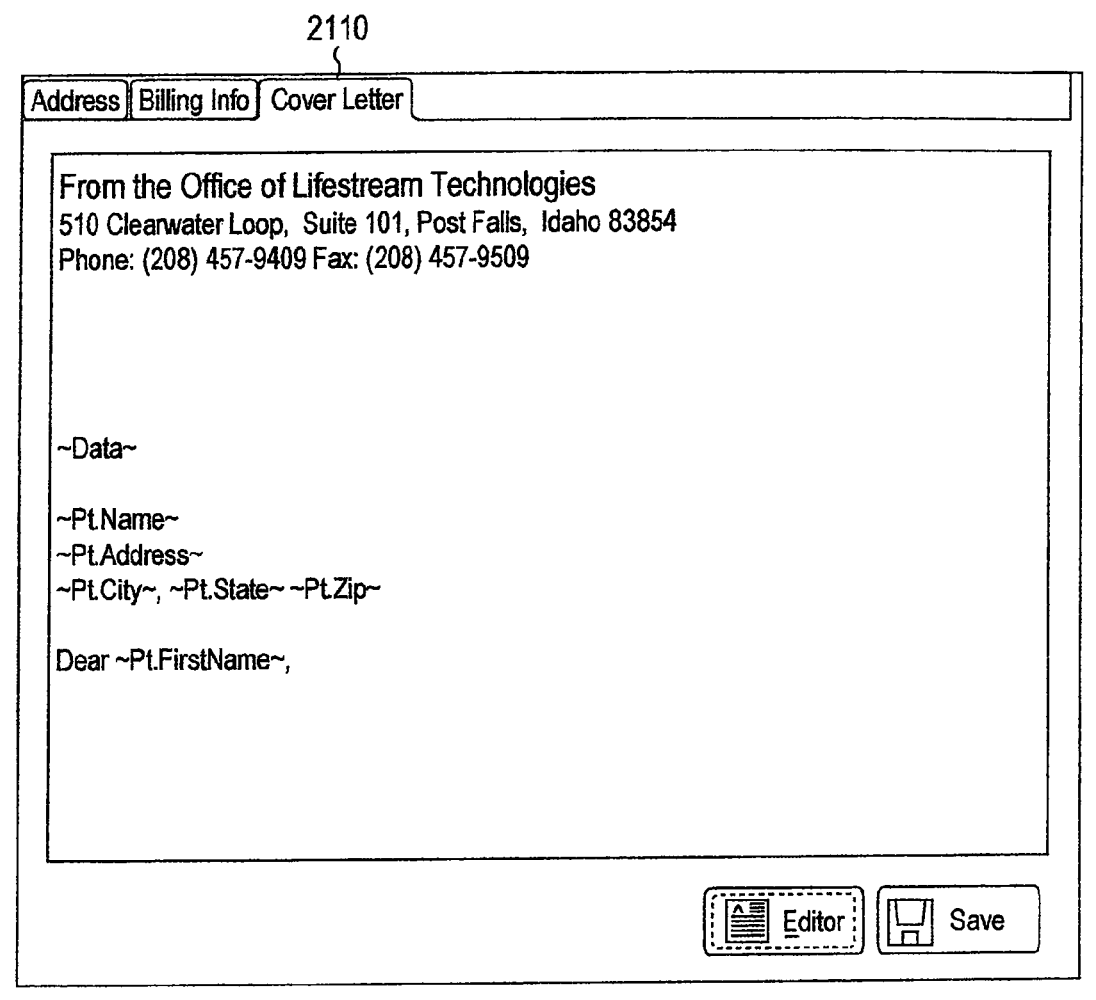

Similarly, step 1712 may be followed by step 1714, in which the PRIVALINK software 1402 displays a "cover letter" user interface 2300 in response to user selection of the "cover letter" tab 2110. FIG. 23 is an illustration of a typical "cover letter" user interface 2300. This interface allows the practitioner to author a cover letter that will be included with a health report booklet to be produced by the booklet generation module 1410 on the server-based system 1400, as described previously with reference to FIG. 9. This allows the practitioner to customize the cover letter for each health report booklet produced by the system.

Figure 24:
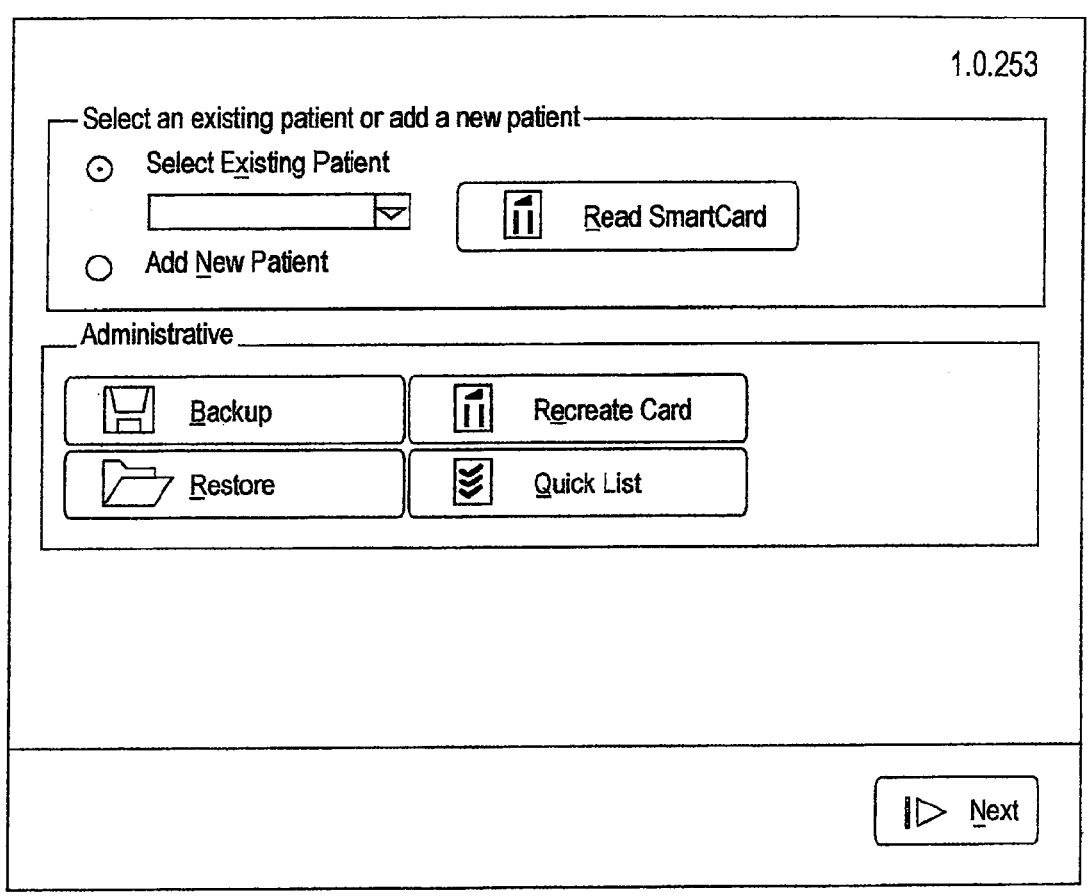
FIG. 24 is an illustration of a "patient selection" user interface in a secure medical records maintenance system.

To further illustrate the operation of the user interface, it is assumed that the practitioner next selects the "patients" selection item 2004 on the "switchboard" user interface 2000. Thus, step 1714 is followed by step 1716, in which the PRIVALINK software 1402 displays a "patients" user interface 2400. FIG. 24 is an illustration of a typical "patient selection" user interface 2400. This user interface allows the practitioner to select a preexisting patient and to enter new patients. Upon entry of a new patient, the PRIVALINK software 1402 typically assigns a unique patient identification number and a unique medical records identification number to the patient, which the user site "PRIVALINK" software 1402 stores in a correlation table 1600, as described previously with reference to FIG. 16.

Figure 25:
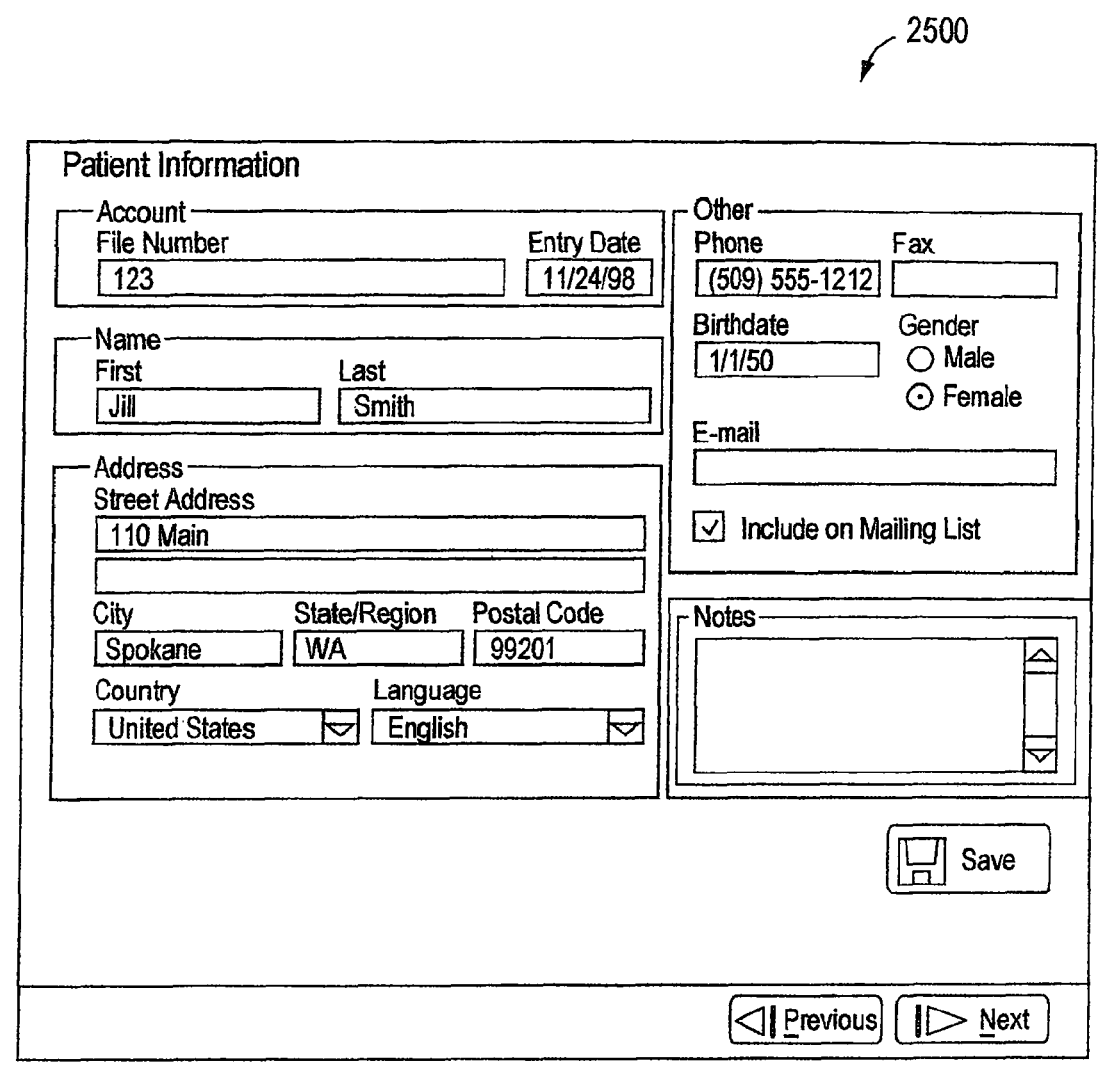

Step 1716 is followed by step 1718, in which the PRIVALINK software 1402 displays a "patient information" user interface 2500. FIG. 25 is an illustration of a typical "patient information" user interface 2500. This interface includes a number of fields for entering patient identification information, such as address, phone number, and so forth. As described previously with reference to FIG. 16, this patient identification information is typically indexed by the patient identification number and stored in the first server 1404, whereas the patient's medical data is typically indexed by the patient's medical records identification number and stored in the second server 1406.

Step 1718 is followed by step 1720, in which the PRIVALINK software 1402 displays a "questionnaire data" user interface 2600. FIG. 26 is an illustration of a typical "questionnaire data" user interface 2600. This interface includes a number of fields for entering patient diagnostic information, such as family history, age, weight, body fat, and so forth. This interface may be used to enter patient diagnostic information in addition to that received through the meter 10. For example, the interface 2600 may be used to enter diagnostic data that the meter would have recorded, but the patient failed to enter the data into the meter 10. In addition, the interface 2600 may be automatically filled in, either partially or completely, with the appropriate data stored on a corresponding smartcard 54. This step may require entry of an appropriate patient PIN for the corresponding smartcard 54 into the interface 2600. The interface 2600 may also be used to change or supplement the data read from the smartcard 54, or enter additional diagnostic information that the meter 10 is not configured to collect from the patient.

Figure 27:
FIG. 27 is an illustration of a "generate reports" user interface in a secure medical records maintenance system.

Step 1720 is followed by step 1722, in which the PRIVALINK software 1402 displays a "generate reports" user interface 2700. FIG. 27 is an illustration of a typical "generate reports" user interface 2700. This interface includes a number of fields for selecting items to be included in a patient's health report booklet, such as cover letter, summary, evaluation, and so forth. The interface includes a number of fields for selecting therapy items to be prescribed for the patient and reflected in the patient's health report booklet, such as lifestyle therapy, lipid drug prescription, blood pressure drug prescription, and so forth.

FIG. 28 is an illustration of typical health report charts generated by the secure medical records maintenance system 1400 for inclusion in a patient's health report booklet. These charts include a "coronary risk factors" chart 2802, a "personal health consequences" chart 2804, and an "extended health assessment" chart 2806. The "coronary risk factors" chart 2802 includes test results and diagnostic information along with ideal ranges and patient goals for these items. The "personal health consequences" chart 2804 includes interpretive data, such as pounds overweight, cardiac age, and stroke risk. The "extended health assessment" chart 2806 includes a projection of future interpretive data, such as a projected comparison of the patient's chronological age and cardiac age.

Figure 29:
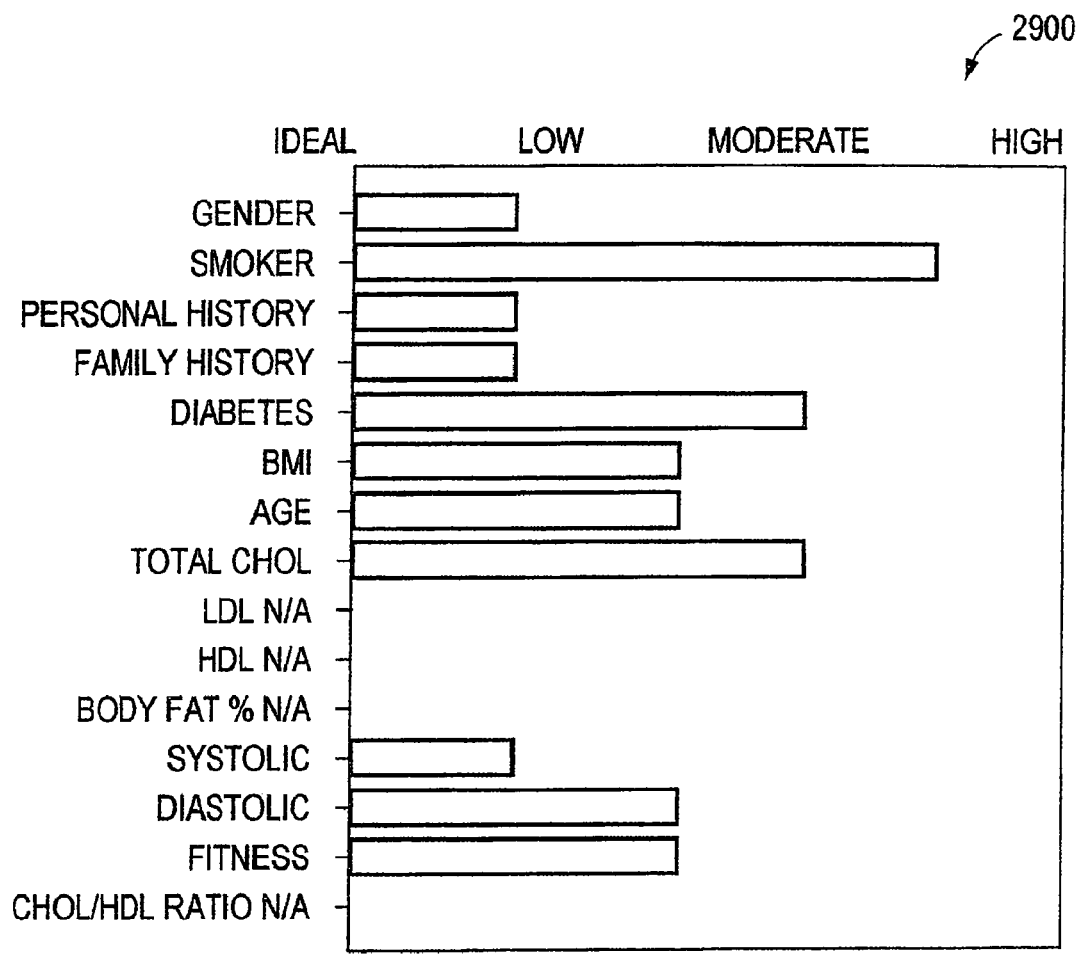
FIG. 29 is an illustration of an additional health assessment chart generated by a secure medical records maintenance system.

FIG. 29 is an illustration of an additional health assessment chart 2900 generated by the secure medical records maintenance system 1400 for inclusion in a patient's health report booklet. This chart includes a pictorial representation of cardiac risk factors, such as gender, smoker, personal history, and so forth. The health assessment chart 2900 typically presents a pictorial assessment of the "coronary risk factors" shown in chart 2802.

Smartcard Payment System

The system described above is largely dependent on the sale of proprietary test strips 28 for the collection of revenue from end users. That is, the meter 10 may be made available to individual patients at little or no cost, with the sale of proprietary test strips 28 providing a major source of revenue for the proprietor of the health monitoring meter. This may be a desirable business model for deploying the meters 10 because it minimizes the initial cost that an individual patient must pay to begin using the device. Having to sell each meter 10 at its full cost, on the other hand, would undermine the economic feasibility of using the meter in many contexts.

Nevertheless, it may also be desirable to provide a meter 10 that does not rely on the sale of proprietary test strips 28 as a major source of revenue. For example, the meter may be adapted to read non-proprietary test strips, or may incorporate a reusable and/or non-invasive testing device, such as an electrode, blood pressure monitoring device, sonic testing device, thermometer, saliva testing device, optical testing device, and the like. Of course, a non-invasive multi-use testing device may be used many times without affording the proprietor of the health monitoring device an opportunity collect revenue associated with use of the device.

To solve this problem, the smartcard 54 may be utilized as a type of "debit card" for use with the meter 10. That is, the smartcard 54 device may be purchased with a monetary value, or it may have a monetary value that is replenishable over the Internet using a bank credit or debit card or other conventional payment source. The meter 10 may then deduct the cost of performing particular services (e.g., blood cholesterol test, health assessment, blood sugar test, AIDS test, etc.) from the monetary value represented by the monetary balance stored on the smartcard 54. In other words, the meter 10 may be configured to activate for the performance of a variety of services upon deducting a charge for the selected service from a monetary value stored on a smartcard 54 inserted into the device.

Figure 30:
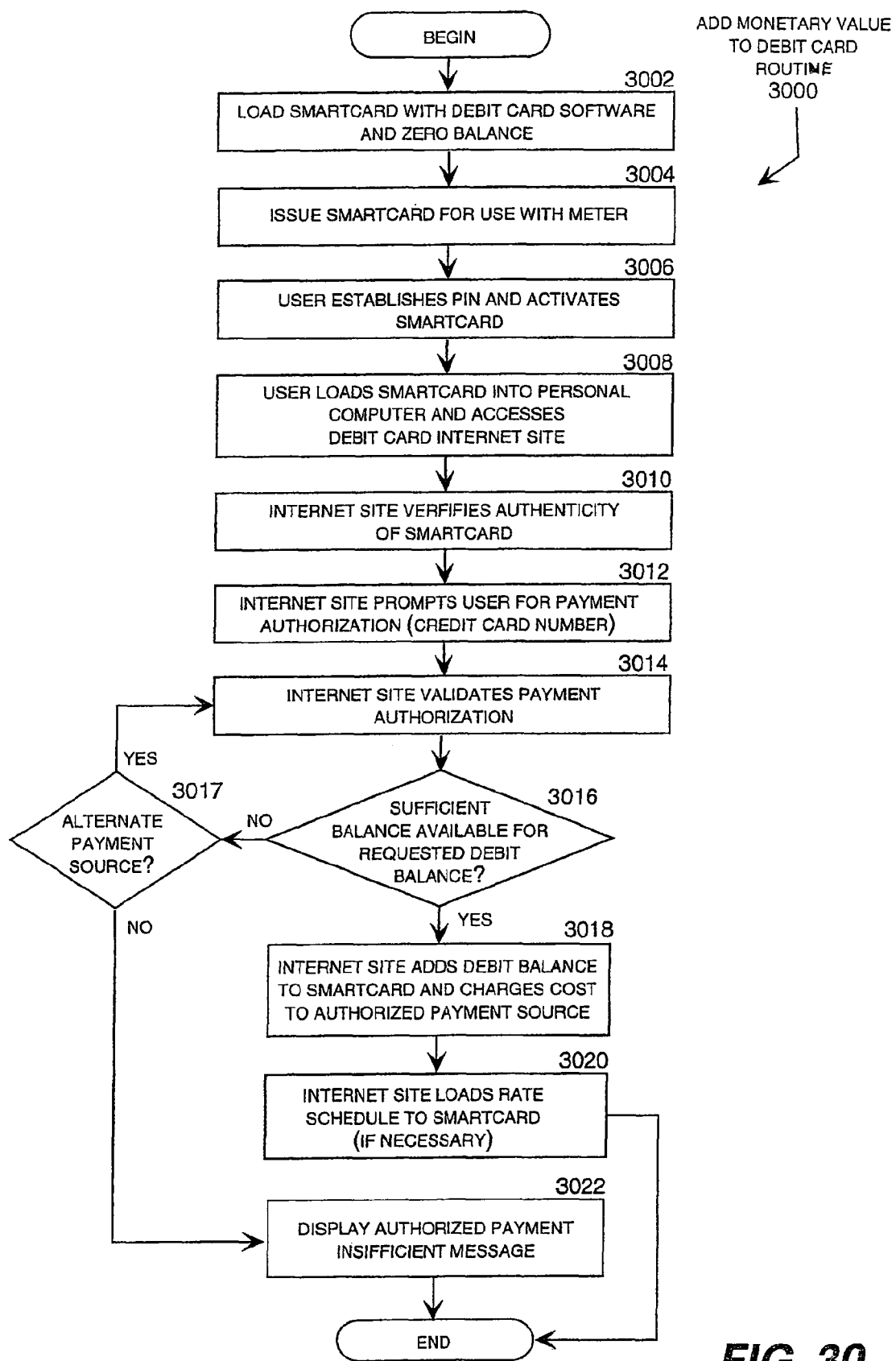
FIG. 30 is a logic flow diagram illustrating a routine for adding a monetary value to a smartcard for use with a health monitoring device.

FIG. 30 is a logic flow diagram illustrating a routine 3000 for adding a monetary value to a smartcard 54 for use with the meter 10. Although single-use smartcard could be sold with a monetary value for use with the meter 10, the cost of the smartcards makes a replenishable debit card system preferable. In step 3002, the proprietor of the system loads an illustrative smartcard 54 with debit card software and a zero balance. Step 3002 is followed by step 3004, in which the smartcard 54 is issued for use with the meter 10. For example, the smartcard 54 may be sold or given away separately or in connection with a meter 10. Typically, the proprietor of the system will be motivated to make both the meter 10 and the smartcard 54 available for little or no acquisition cost because the cost of these assets will be recovered through use of the debit-card type smartcard 54 with meter 10.

Step 3004 is followed by step 3006, in which the user establishes a PIN and activates the smartcard 54, which can be performed using the meter 10 or a conventional computer 108 having a smartcard interface 106, as shown in FIG. 2. Step 3006 is followed by step 3008, in which the user loads the smartcard 54 into a conventional computer 108 having a smartcard interface 106 (if the smartcard in not already loaded) and accesses a predefined debit card Internet site by linking to an associated URL, which may be printed on the smartcard or made available through advertisement, direct mail, or other communication media. The debit card Internet site may typically be a separate server operated by the proprietor of the secure medical records maintenance system 1400, or it may be another site operated by a separate proprietor. Step 3008 is followed by step 3010, in which the debit card Internet site establishes communications with the smartcard 54 and verifies the authenticity of the smartcard.

Step 3010 is followed by step 3012, in which the debit card Internet site prompts the user for input payment authorization for a monetary value to be added to the smartcard. The debit card Internet site may accept a variety of payment options, such as a bank credit or debit card number, a bank account number for wire transfers, authorization to include the charges on a telephone bill or Internet service provider bill associated with the Internet link, and the like. Step 3012 is followed by step 3014, in which the debit card Internet site validates the received payment authorization. Step 3014 is followed by step 3016, in which the debit card Internet site determines whether the received authorized payment source has a sufficient balance or credit limit for the monetary value that the user has requested for addition to the smartcard 54.

If the authorized payment source has a sufficient balance or credit limit, the "YES" branch is followed to step 3018, in which the debit card Internet site adds the requested monetary value to the smartcard 54 and charges the cost to the authorized payment source. Optionally, the debit card Internet site may also load a rate schedule for services to be provided by the meter 10 onto the smartcard 54. In this case, the meter 10 reads the monetary value assigned to performance of the test from the smartcard 54. Thus, rate schedules for various services to be performed by the meter 10 may be changed from time to time, based on quantity discounts or other considerations. Step 3020 is followed by the "END" step, which concludes routine 3000.

Referring again to step 3016, if the payment source is invalid or does not have a sufficient balance or credit limit, the "NO" branch is followed to step 3017, in which the user is prompted for another payment source. If the user enters another payment source, the "YES" branch loops to step 3014 for validation of the alternate payment source. If the user does not enter another payment source, the "NO" branch is followed by the "END" step, which concludes routine 3000.

Figure 31:
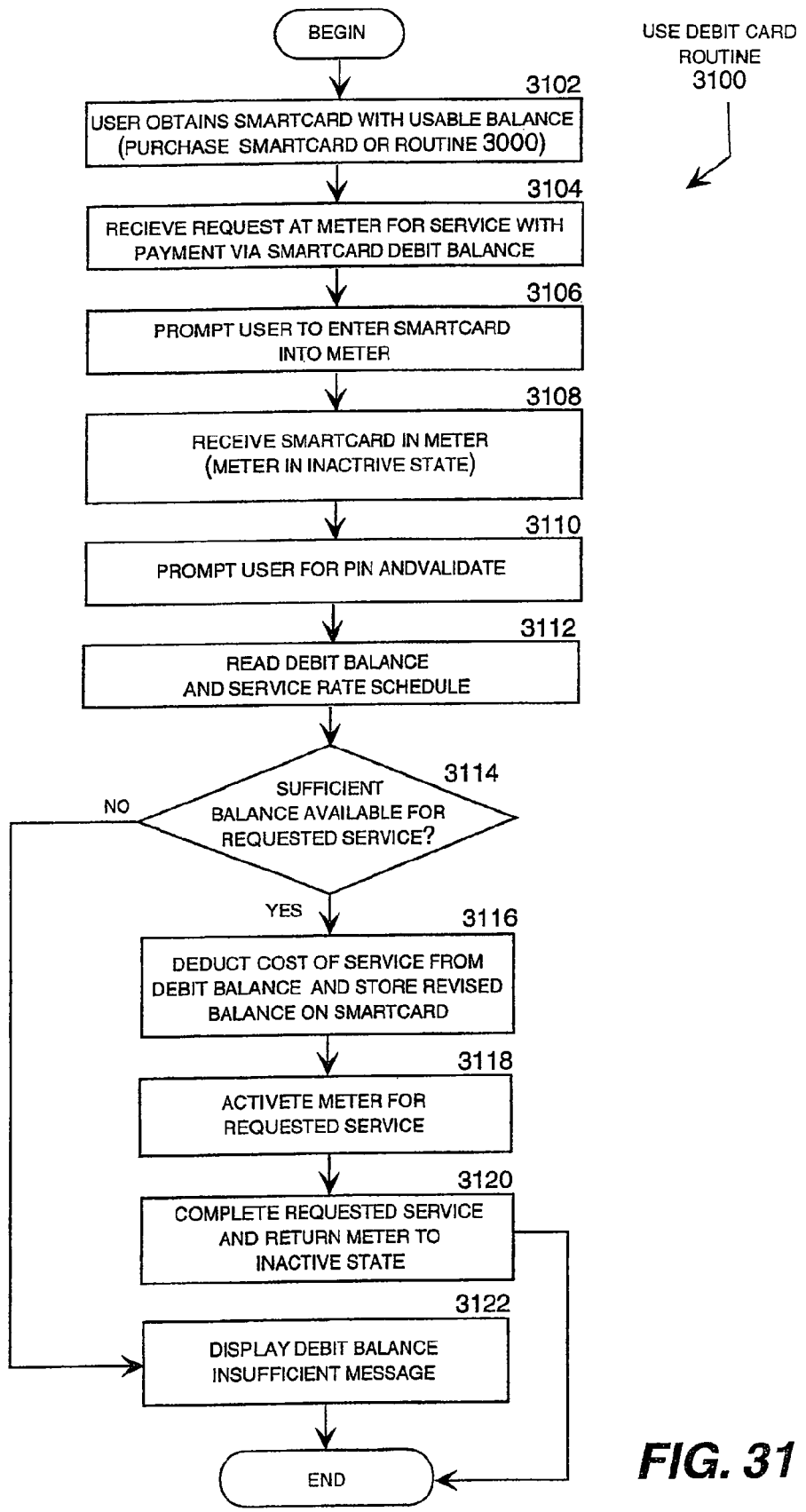
FIG. 31 is a logic flow diagram illustrating a routine for using a smartcard to pay for a service provided by a health monitoring device.

FIG. 31 is a logic flow diagram illustrating a routine 3100 for using a smartcard 54 to pay for a service provided by the meter 10. In step 3102, a user obtains a smartcard 54 with a usable monetary value, typically by purchasing a smartcard having a usable monetary value or by adding a monetary value to a smartcard as described with reference to FIG. 30. Step 3102 is followed by step 3104, in which the meter 10 receives a request to provide a service, such as a blood cholesterol test and/or production of a health report, with the associated cost to be charged against a monetary value stored on the smartcard 54. Step 3104 is followed by step 3106, in which the meter 10 prompts the user to enter a smartcard 54 with a usable monetary value into the meter. Step 3106 is followed by step 3108, in which the meter 10 receives the smartcard 54 in the reader 50. It should be understood that at this point the meter is inactive for performing services that require payment. Note also that the meter 10 may be activated alternatively through proprietary test strip validation, as described with reference to FIG. 6.

Step 3110 is followed by step 3112, in which the meter 10 prompts the user for a PIN for use with the smartcard 54 and validates the PIN (i.e., checks the received PIN against the PIN stored on the smartcard). If the PIN is validated, step 3112 is followed by step 3114, in which the meter 10 determines whether the monetary value stored on the smartcard 54 is sufficient to pay for the requested service. As noted previously, the meter 10 may also read the rate schedule from the smartcard 54. Alternatively, if no rate schedule is present on the smartcard 54, the meter 10 may use a predefined "default" rate schedule for the requested service.

If the monetary value stored on the smartcard 54 is sufficient to pay for the requested service, the "YES" branch is followed to step 3116, in which the meter 10 deducts the cost for the requested service from the monetary value stored on the smartcard 54. That is, the meter 10 computes a revised monetary balance equal to the initial monetary value stored on the smartcard less the cost for the requested service, and replaces the initial monetary value stored on the smartcard with the revised monetary balance. Step 3116 is followed by step 3118, in which the meter 10 activates for performance of the requested service. Step 3118 is followed by step 3120, in which the meter 10 completes the requested service and returns to the inactive state. Referring again to step 3114, if the monetary value stored on the smartcard 54 is insufficient to pay for the requested service, the "NO" branch is followed to step 3122, in which the meter displays a "balance insufficient" message. Steps 3120 and 3122 are followed by the "END" step, which concludes routine 3100.

The present invention thus provides a health monitoring and diagnostic device (LIFESTREAM cholesterol meter) that works in connection with a network-based comprehensive health analysis and reporting system. The invention also provides a secure medical records maintenance system that works in conjunction with the health monitoring and diagnostic device, and alternative business models for deploying the health monitoring and diagnostic devices. It should be understood that the foregoing pertains only to the preferred embodiments of the present invention, and that numerous changes may be made to the embodiments described herein without departing from the spirit and scope of the invention.

The invention claimed is:

1. A system for remotely producing health reports, comprising:
   a health monitoring device including:
      a test strip reader operable for reading a test strip carrying a sample of biological fluid or tissue and obtaining test results based on the sample of biological tissue or fluid and calibration data specific to the test strip, wherein the test strip reader is operable for reading a second type of test strip carrying a second sample of biological fluid or tissue and obtaining health-related test results based on the second sample of biological tissue or fluid and calibration data specific to the second type of test strip, further comprising: a second memory reading device functionally connected to the test strip reader and operable for reading calibration data from a second memory device corresponding to the second type of test strip,
      a memory reading device functionally connected to the test strip reader and operable for reading the calibration data from a memory device, and
      a data drive functionally connected to the test strip reader and operable for writing the test results to a memory storage device;
   a health report server operable for:
      receiving the test results and additional diagnostic information,
      compiling a health report based on the test results and the additional diagnostic information, said health report including one or more of the following data items: a five-year risk of heart attack, a ten-year risk of heart attack, a cardiac age, an extended age, or a risk of stroke, and
      transmitting the health report; and
   a computer station operable for:
      reading the test results from the memory storage device,
      establishing a network connection with the health report server,
      receiving the additional diagnostic information,
      transmitting the test results and the additional diagnostic information to the health report server,
      receiving the health report from the health report server, and
      printing the health report.

2. The system for remotely producing health reports of claim 1, wherein the health report includes a trend analysis including test results compiled for a number of samples of the biological fluid or tissue.

3. The system for remotely producing health reports of claim 1, wherein:
   the biological fluid or tissue includes a droplet of human blood;
   the test results include blood lipid levels; and
   the additional diagnostic information includes one or more of the following data items corresponding to a person providing the droplet of human blood: gender, ethnicity, family history of heart disease, personal history of heart disease, personal history of diabetes, personal history of smoking, height, weight, age, blood pressure, and fitness level.

4. The system for remotely producing health reports of claim 1, wherein:
   the health report includes one or more of the following data items: a medical risk index and a recommended weight loss.

5. The system for remotely producing health reports of claim 4, wherein:
   the additional diagnostic information includes a newly-prescribed drug and other currently-prescribed drugs; and
   the health report includes a data sheet for the newly-prescribed drug and information relating to cross-reactions between the newly-prescribed drug and the other currently-prescribed drugs.

6. The system for remotely producing health reports of claim 5, wherein the health report further includes one or more of the following items:
   target weight and blood lipid levels;
   a schedule for future testing using the health monitoring device;
   a health assessment summary;
   a coronary risk assessment; and
   dietary guidelines to lower cholesterol.

7. The system for remotely producing health reports of claim 1 wherein:
   the test results include blood glucose levels; and
   the health report further includes a trend analysis including test results compiled for a number of samples of the biological fluid or tissue.

8. The system of claim 1 wherein the health monitoring device further includes a secure data system for maintaining the security of the test results.

* * * * *

UNITED STATES PATENT AND TRADEMARK OFFICE
CERTIFICATE OF CORRECTION

| | | Page 1 of 1 |
|---|---|---|
| PATENT NO. | : 7,767,149 B2 | |
| APPLICATION NO. | : 10/649293 | |
| DATED | : August 3, 2010 | |
| INVENTOR(S) | : Christopher T. Maus et al. | |

It is certified that error appears in the above-identified patent and that said Letters Patent is hereby corrected as shown below:

On the Title Sheet, item (62), instead of:

Division of application No. 09/436,323, filed on Nov. 8, 1999, now Pat. No. 6,602,469.

the text should read:

Division of application No. 10/460,002, filed on June 12, 2003, now abandoned; which is a division of application No. 09/436,323, filed on Nov. 8, 1999, now Pat. No. 6,602,469.

In the Specification, at column 1, line 8, instead of:

This application is a divisional of U.S. patent application Ser. No. 09/436,323 filed Nov. 8, 1999, now U.S. Pat. No. 6,602,469 issued Aug. 5, 2003; which claims the benefit of commonly-owned U.S. Provisional Patent Application No. 60/107,707, filed Nov. 9, 1998; and commonly-owned U.S. Provisional Patent Application No. 60/144,705, filed Jul. 20, 1999.

the text should read:

This application is a divisional of U.S. patent application Ser. No. 10/460,002 filed June 12, 2003, now abandoned, which is a divisional of Ser. No. 09/436,323 filed Nov. 8, 1999, now U.S. Pat. No. 6,602,469 issued Aug. 5, 2003; which claims the benefit of commonly-owned U.S. Provisional Patent Application No. 60/107,707, filed Nov. 9, 1998; and commonly-owned U.S. Provisional Patent Application No. 60/144,705, filed Jul. 20, 1999.

Signed and Sealed this
Twentieth Day of January, 2015

Michelle K. Lee
*Deputy Director of the United States Patent and Trademark Office*